United States Patent
Murphy et al.

(10) Patent No.: US 10,877,018 B2
(45) Date of Patent: Dec. 29, 2020

(54) METHODS FOR DETERMINING CHEMICAL HETEROGENEITY OF GLASS CONTAINERS

(71) Applicant: CORNING INCORPORATED, Corning, NY (US)

(72) Inventors: Kelly Ann Murphy, Phoenixville, PA (US); Robert Anthony Schaut, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 597 days.

(21) Appl. No.: 15/782,707

(22) Filed: Oct. 12, 2017

(65) Prior Publication Data
US 2018/0100846 A1    Apr. 12, 2018

Related U.S. Application Data

(60) Provisional application No. 62/407,321, filed on Oct. 12, 2016.

(51) Int. Cl.
| | | |
|---|---|---|
| *G01N 33/38* | (2006.01) | |
| *G01N 17/00* | (2006.01) | |
| *A61J 1/14* | (2006.01) | |
| *G01N 1/32* | (2006.01) | |
| *C03C 15/00* | (2006.01) | |

(52) U.S. Cl.
CPC ........... *G01N 33/386* (2013.01); *A61J 1/1468* (2015.05); *C03C 15/00* (2013.01); *G01N 1/32* (2013.01); *G01N 17/00* (2013.01)

(58) Field of Classification Search
CPC ........ G01N 33/386; G01N 1/32; G01N 17/00; C03C 15/00; A61J 1/1468
See application file for complete search history.

(56) References Cited

U.S. PATENT DOCUMENTS

| | | |
|---|---|---|
| 9,322,766 B2 | 4/2016 | Scheumann et al. |
| 9,346,707 B2 | 5/2016 | Danielson et al. |
| 2013/0059069 A1* | 3/2013 | Aoyagi ............... G01N 33/386 427/165 |

(Continued)

OTHER PUBLICATIONS

International Search Report & Written Opinion dated Jan. 9, 2018, for PCT/US2017/056390 filed Oct. 12, 2017. pp. 1-13.

(Continued)

*Primary Examiner* — Xin Y Zhong
(74) *Attorney, Agent, or Firm* — Dinsmore & Shohl LLP

(57) ABSTRACT

A method including obtaining glass containers, and adding a solvent to 5.0% by volume to less than or equal to 50.0% by volume. Heating to an elevated temperature and cooling to room temperature. The solvent is consolidated and titrated, where an amount of a titrant is an as received titrant volume. Glass containers are etched, and a second solvent is added at 8.0% by volume to less than or equal to 25.0% by volume. The containers are heated to an elevated temperature and cooled to room temperature. The second solvent is consolidated and titrated, where an amount of a titrant is an etched titrant volume. The Chemical Durability Ratio (CDR) of the plurality of glass containers is calculated where:

$$CDR = \frac{\text{As Received Titrant Volume}}{\text{Etched Titrant Volume}}.$$

34 Claims, 5 Drawing Sheets

(56) References Cited

U.S. PATENT DOCUMENTS

| | | |
|---|---|---|
| 2013/0327740 A1 | 12/2013 | Adib et al. |
| 2014/0151370 A1 | 6/2014 | Chang et al. |
| 2014/0240694 A1* | 8/2014 | Scheumann .......... G01N 21/91 |
| | | 356/36 |
| 2016/0107924 A1* | 4/2016 | Yamamoto .............. C03C 3/085 |
| | | 501/67 |
| 2016/0145150 A1 | 5/2016 | Bookbinder et al. |

OTHER PUBLICATIONS

Nn: "<660> Containers-Glass", Jul. 5, 2015 (Jul. 5, 2015) XP55437217, [Retrieved from the Internet on Dec. 21, 2017], <URL: https://hmc.usp.org/sites/default/files/documents/HMC/GCs-Pdfs/c660.pdf>. pp. 1-7.

Hunt, Briefing "1660 Evaluation of the Inner Surface Durability of Glass Containers", Apr. 17, 2012 (Apr. 17, 2012), XP55437172, [Retrieved from the Internet on Dec. 20, 2017], <URL: http://www.uspnf.com/sites/default/files/usp_pdf/EN/USPNF/revisions/c1660.pdf>. pp. 1-9.

U.S. Department of Health & Human Services, "Advisory to Drug Manufactures: Formation of Glass Lamellae in Certain Injectable Drugs" [online] U.S. Food & Drug Administration, Mar. 25, 2011, retrieved from the internet: <URL: http://www.fda.gov/Drugs/DrugSafety/ucm248490.htm>.

\* cited by examiner

METHODS FOR DETERMINING CHEMICAL HETEROGENEITY OF GLASS CONTAINERS

CROSS REFERENCE TO RELATED APPLICATIONS

The present specification claims priority to U.S. Provisional Patent Application Ser. No. 62/407,321 filed Oct. 12, 2016 and entitled "Methods for Determining Chemical Heterogeneity of Glass Containers," the entirety of which is incorporated by reference herein.

BACKGROUND

Field

The present specification generally relates to determining the degree of heterogeneity in glass packaging. More specifically, the present specification is directed to methods and apparatuses for determining the degree of heterogeneity in pharmaceutical glass packaging.

Technical Background

Historically, glass has been used as the preferred material for packaging pharmaceuticals because of its hermeticity, optical clarity, and excellent chemical durability relative to other materials. Specifically, the glass used in pharmaceutical packaging must have adequate chemical durability so as to not affect the stability of the pharmaceutical compositions contained therein. Glasses having suitable chemical durability include those glass compositions within the ASTM standard E438.92 'Type IA' and 'Type IB' glass compositions or glass compositions defined as Type I compositions by the USP <660> (hereinafter referred to as "Type I"), which have a proven history of chemical durability. In general terms, chemically durable glasses are glasses whose constituent components do not dissolve from the glass when the glass is exposed to a solution for extended periods of time. However, even chemically durable glass compositions have a tendency to delaminate or shed glass particles following exposure to pharmaceutical solutions.

The primary factor that contributes to the delamination of glass containers is the chemical heterogeneity of the glass containers. Certain chemical species have a lower volatilization temperature, which causes them to volatilize during formation of the glass container. These species may then be deposited in higher quantities on certain regions of the glass container interior; resulting in chemical heterogeneity of the glass container. Additionally, the removal of volatile species from the glass surface can result in chemical heterogeneity. The regions of the glass containers where these volatilized species have been deposited and incorporated into the glass surface or regions where volatile species have been removed from the glass surface have reduced durability and are enriched with the volatile species, which react with the contents of the container to a higher extent than other species in the glass composition. As a result, the amount of glass corrosion in these regions is enhanced. The loss of sodium borates from the enriched region leaves behind a skin that is primarily silica. This silica skin is lost as a delamination flake. This is most commonly observed in the heel or lower sidewall of the glass containers.

Conventional methods for measuring heterogeneity of glass containers, such as DSIMS and XPS, are costly and do not sample enough of the glass container surface area to be representative of the drug-contacting area. Conventional methods for investigating the delamination mechanism, such as USP <1660>, involve uncertain responses and long lead times. In addition, conventional tests for chemical durability, such as USP <1660> involve filling the glass containers to 90% filled with a substance, such as a glycine solution, and allowing the solution to react with the glass container over time. Such tests require the glass container to be completely filled with the substance and can take an extended period of time to achieve reliable results. For some methods, it can take eight months or longer to achieve reliable results. Because the chemical heterogeneity, which leads to delamination, may be caused by localized manufacturing conditions, sampling is not necessarily adequate to ensure that produced glass containers will not be prone to delamination because the absence of flakes, or lamellae, in one sample does not necessarily guarantee the absence of flakes, or lamellae, in another sample. With lead times of eight months or more and the requirement that the glass container be nearly completely filled with a substance, testing every glass container with conventional testing methods is not a commercially viable option.

Accordingly, a need exists for apparatuses and processes to measure the chemical heterogeneity of the glass containers that do not require eight or more months to achieve reliable results and also do not require the glass containers to be completely filled with a substance, such as glycine.

SUMMARY

Embodiments disclosed herein describe a method for determining a delamination risk of a plurality of glass containers. The method includes obtaining a plurality of glass containers, each glass container of the plurality of glass containers having a similar composition and similar geometry, and adding to each glass container of the plurality of the glass containers a solvent such that a volume of the solvent in each glass container comprises from greater than or equal to 5.0% by volume of the glass container to less than or equal to 50.0% by volume of the glass container. Then, the plurality of glass containers are heated to a temperature from 90° C. to 130° C. and then the plurality of glass containers are cooled to room temperature. The method further includes removing and consolidating the solvent from the plurality of glass containers to obtain a consolidated solvent and titrating the consolidated solvent, where an amount of a titrant used in titrating the consolidated solvent is an as received titrant volume. Subsequently, the plurality of glass containers are etched by contacting at least an interior surface of the glass container with an etchant, where the etching removes a layer of the interior surface of each glass container, the layer having a thickness from greater than or equal to 0.75 μm to less than or equal to 15 μm to obtain a plurality of etched glass containers and then rinsing each etched glass container of the plurality of etched glass containers to remove residual etchant. Then, a second solvent is added to each etched glass container of the plurality of etched glass containers such that a volume of the second solvent in each etched glass container comprises from greater than or equal to 5.0% by volume of the etched glass container to less than or equal to 50.0% by volume of the etched glass container, and the plurality of etched glass containers to are heated to temperatures from 90° C. to 130° C. and cooled to room temperature. The second solvent is removed from the plurality of etched glass containers and consolidated to obtain an etched consolidated solvent. Then, the method includes titrating the etched consolidated solvent, where an amount of a titrant used in titrating the etched consolidated solvent is an etched titrant volume. Finally, the Chemical Durability Ratio (CDR) of the plurality of glass containers is calculated where:

$$CDR = \frac{\text{As Received Titrant Volume}}{\text{Etched Titrant Volume}}.$$

In another embodiment, a method for determining a delamination risk of a plurality of glass containers is described. The method includes obtaining a plurality of glass containers, each glass container of the plurality of glass containers having a similar composition and similar geometry, and adding to each glass container of the plurality of the glass containers a solvent such that a volume of the solvent in each glass container comprises from greater than or equal to 8.0% by volume of the glass container to less than or equal to 25.0% by volume of the glass container. Further, each container of the plurality of the glass containers is plugged with a water tight plug, and each container of the plurality of the glass containers is inverted. Then, the method includes heating the plurality of glass containers to a temperature from 90° C. to 130° C., and cooling the plurality of glass containers to room temperature. Subsequently, the solvent from the plurality of glass containers is removed and consolidated to obtain a consolidated solvent, and the consolidated solvent is titrated, where an amount of a titrant used in titrating the consolidated solvent is an as received titrant volume. The method also includes etching each glass container of the plurality of glass containers by contacting at least an interior surface of each glass container with an etchant, where the etching removes a layer of the interior surface of each glass container, the layer having a thickness from greater than or equal to 0.75 µm to less than or equal to 15 µm to obtain a plurality of etched glass containers. Each etched glass container of the plurality of etched glass containers is rinsed to remove residual etchant, and the method includes adding to each etched glass container of the plurality of etched glass containers a second solvent such that a volume of the second solvent in each etched glass container comprises from greater than or equal to 8.0% by volume of the etched glass container to less than or equal to 25.0% by volume of the etched glass container. Subsequently, each container of the plurality of the glass containers is plugged with a water tight plug, and is inverted. The plurality of etched glass containers are heated to temperatures from 90° C. to 130° C., and cooled to room temperature. The method then includes removing and consolidating the second solvent from the plurality of etched glass containers to obtain an etched consolidated solvent, and titrating the etched consolidated solvent, wherein an amount of a titrant used in titrating the etched consolidated solvent is an etched titrant volume. Finally, the Chemical Durability Ratio (CDR) of the plurality of glass containers is calculated, where:

$$CDR = \frac{\text{As \textit{Recieved} Titrant Volume}}{\text{Etched Titrant Volume}}.$$

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
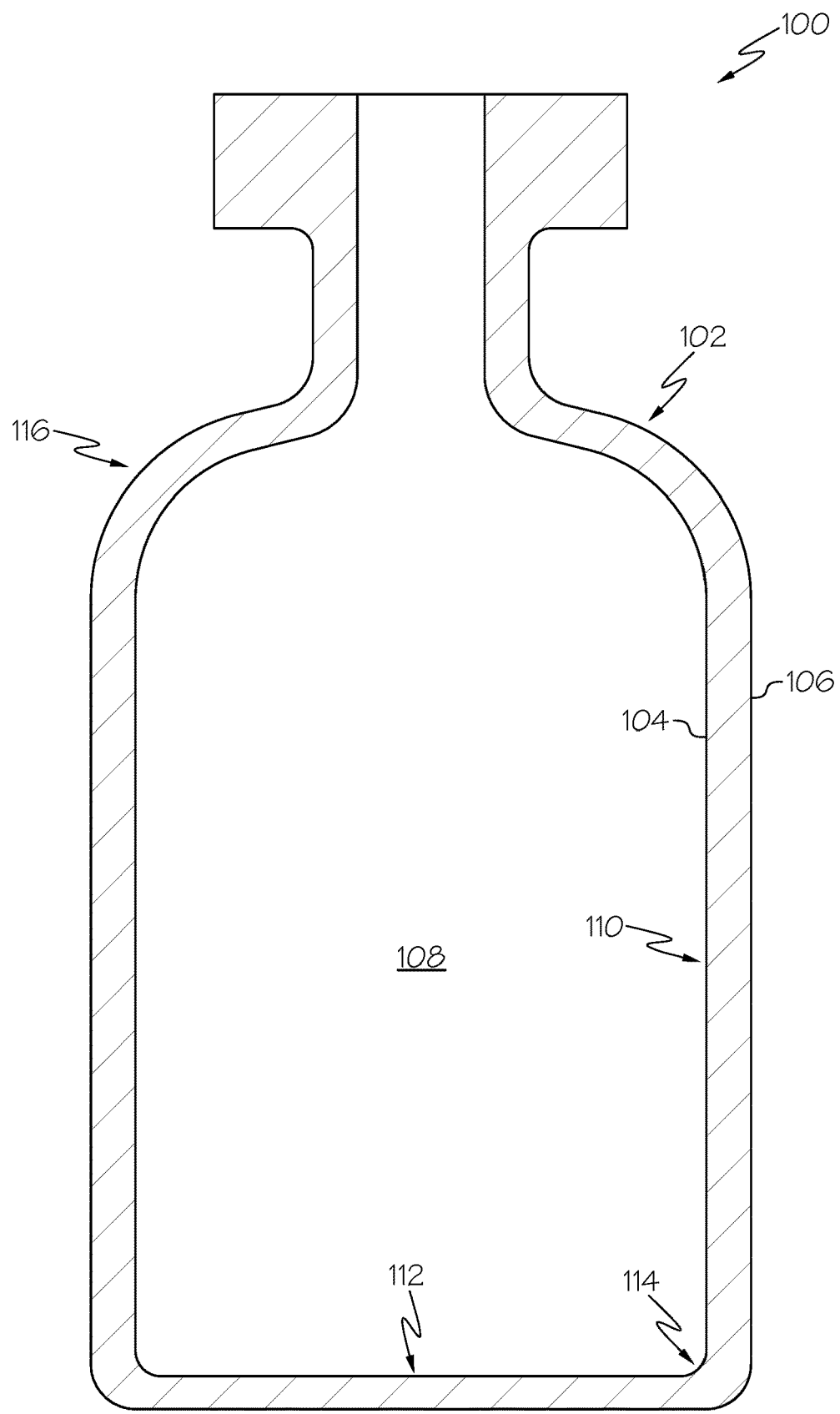
FIG. 1 schematically depicts a cross section of a glass container, specifically a glass vial, according to one or more embodiments described herein.

Reference will now be made in detail to various embodiments of apparatuses and methods for measuring the heterogeneity of glass containers, such as glass vials, examples of which are illustrated in the accompanying drawings. Whenever possible, the same reference numerals will be used throughout the drawings to refer to the same or like parts. In one embodiment, a method for determining a delamination risk of a plurality of glass containers, including: obtaining a plurality of glass containers, each glass container of the plurality of glass containers having a similar composition and similar geometry; adding to each glass container of the plurality of the glass containers a solvent such that a volume of the solvent in each glass container comprises from greater than or equal to 5.0% by volume of the glass container to less than or equal to 50.0% by volume of the glass container; heating the plurality of glass containers to a temperature from 90° C. to 130° C.; cooling the plurality of glass containers to room temperature; removing and consolidating the solvent from the plurality of glass containers to obtain a consolidated solvent; adding an indicator to the consolidated solvent; titrating the consolidated solvent, wherein an amount of a titrant used in titrating the consolidated solvent is an as received titrant volume; etching each glass container of the plurality of glass containers by adding an etchant to each glass container, wherein the etching removes a layer of an interior surface of each glass container, the layer having a thickness from greater than or equal to 0.75 µm to less than or equal to 15.0 µm to obtain a plurality of etched glass containers; rinsing each etched glass container of the plurality of etched glass containers to remove residual etchant; adding to each etched glass container of the plurality of etched glass containers a second solvent such that a volume of the second solvent in each etched glass container comprises from greater than or equal to 5.0% by volume of the etched glass container to less than or equal to 50.0% by volume of the etched glass container; heating the plurality of etched glass containers to temperatures from 90° C. to 130° C.; cooling the plurality of etched glass containers to room temperature; removing and consolidating the second solvent from the plurality of etched glass containers to obtain an etched consolidated solvent; titrating the etched consolidated solvent, wherein an amount of a titrant used in titrating the etched consolidated solvent is an etched titrant volume; calculating a Chemical Durability Ratio (CDR) of the plurality of glass containers where:

$$CDR = \frac{\text{As Received Titrant Volume}}{\text{Etched Titrant Volume}}.$$

The term "chemical durability," as used herein, refers to the ability of the glass composition to resist degradation upon exposure to specified chemical conditions. Specifically, the chemical durability of the glass compositions described herein was assessed according to 3 established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; ISO 720:1985 entitled "Glass—Hydrolytic resistance of glass grains at 121 degrees C.—Method of test and classification"; and ISO 719:1985 "Glass—Hydrolytic resistance of glass grains at 98 degrees C.—Method of test and classification." Each standard and the classifications within each standard are described in further detail herein. Alternatively, the chemical durability of a glass composition may be assessed according to USP <660> entitled "Surface Glass Test," and/or European Pharmacopeia 3.2.1 entitled "Glass Containers For Pharmaceutical Use" which assess the durability of the interior surface of the glass.

The methods and apparatuses described herein may be used to measure the chemical heterogeneity of any glass container. In embodiments, the glass container may be a glass vial for holding pharmaceutical compositions.

Glass containers or glass packages for containing pharmaceutical compositions are generally formed from glass compositions that are known to exhibit good chemical durability and low thermal expansion, such as Type IA or Type IB alkali borosilicate glasses. While alkali borosilicate glasses exhibit good chemical durability, container manufacturers have observed silica-rich glass flakes, or lamellae, dispersed in the solution contained in the glass containers. This phenomenon is referred to herein as delamination. Delamination occurs particularly when the solution has been stored in direct contact with the glass surface for long time periods (months to years). Accordingly, a glass which exhibits the highest level of chemical durability as categorized in the above tests may not necessarily be resistant to delamination. Accordingly, glass compositions for glass packaging and processes for making glass packaging that reduce or eliminate delamination are disclosed in, for example, U.S. Patent Application Publication Nos. 2014/0151370 and 2013/0327740, which are incorporated herein by reference in their entirety.

Delamination refers to a phenomenon in which glass particles are released from the surface of the glass following a series of leaching, corrosion, and/or weathering reactions. In general, the particles are silica-rich flakes of glass, or lamellae, which originate from the interior surface of the container as a result of the leaching of modifier ions or weak network formers, such as, for example, boron, into a solution contained within the container. These flakes, or lamellae, may generally be from 1 nm to 2 µm thick with a width greater than about 50 µm. As these flakes, or lamellae, are primarily composed of silica, the flakes, or lamellae, generally do not further degrade after being released from the surface of the glass.

It has previously been hypothesized that delamination is due to phase separation that occurs in alkali borosilicate glasses when the glass is exposed to the elevated temperatures used for reforming the glass into a container shape. However, it is now believed that the delamination of the silica-rich glass flakes, or lamellae, from the interior surfaces of the glass containers is due to the compositional characteristics of the glass container in its as received or as formed condition. Specifically, the high silica content of alkali borosilicate glasses causes the glass to have relatively high melting and forming temperatures. However, the alkali, such as, for example, sodium, and borate components in the glass composition melt and/or vaporize at much lower temperatures. In particular, the borate species in the glass are highly volatile and evaporate from the surface of the glass at the high temperatures necessary to form and reform the glass.

Specifically, glass stock, such as a glass tube or the like, is reformed into glass containers, such as, for example, glass vials or the like, at high temperatures and in direct flames. The high temperatures needed at higher equipment speeds cause the more volatile borate species to evaporate from regions of the surface of the glass. When this evaporation occurs within the interior volume of the glass container, the volatilized borate species are re-deposited in other areas of the glass container surface causing compositional heterogeneities in the glass container surface, particularly with respect to the near-surface regions of the interior of the glass container (i.e., those regions at or directly adjacent to the interior surfaces of the glass container).

Referring to FIG. 1 by way of example, a glass container, such as a glass container for storing a pharmaceutical composition, is schematically depicted in cross section. The glass container 100 generally comprises a glass container with a glass body 102. The glass body 102 extends between an interior surface 104 and an exterior surface 106 and generally encloses an interior volume 108. In the embodiment of the glass container 100 shown in FIG. 1, the glass body 102 generally comprises a wall region 110 and a base region 112. The wall regions 110 and the base region 112 may generally have a thickness in a range from 0.5 mm to 3.0 mm. The wall region 110 transitions into the base region 112 through a heel region 114. While the glass container 100 is depicted in FIG. 1 as having a specific shape form (i.e., a vial), it should be understood that the glass container 100 may have other shape forms, including, without limitation, vacutainers, cartridges, syringes, syringe barrels, ampoules, bottles, flasks, phials, tubes, beakers, or the like.

As noted herein, the glass container 100 may be formed by converting a glass tube into the container shape or molding glass into a container shape, such as a vial. For example, as one end of a glass tube is heated to close the glass tube and form the bottom or base region 112 of the container 100, more highly volatile species, such as borate species and/or alkali species—such as sodium—or the like, may volatilize from the bottom region of the container and be re-deposited elsewhere in the container. The volatilization of material from the base regions of the container is particularly pronounced as these areas of the container undergo the most extensive re-formation and, as such, are exposed to the highest temperatures. As a result, the areas of the container exposed to higher temperatures, such as the base region 112, may have silica-rich surfaces. Other areas of the interior surface 104 of the container which are amenable to deposition of the volatilized species, such as the heel region 114, may have an interior surface layer 105 (schematically depicted in FIG. 2) formed by the condensation of the volatilized species and, as such, the surface is enriched with volatile species, such as, for example, sodium and boron. For example, in the case of borate species, areas amenable to boron deposition which are at a temperature greater than the anneal point of the glass composition but less than the hottest temperature that the glass is subjected to during reformation can lead to boron incorporation on the surface of the glass.

Figure 2:
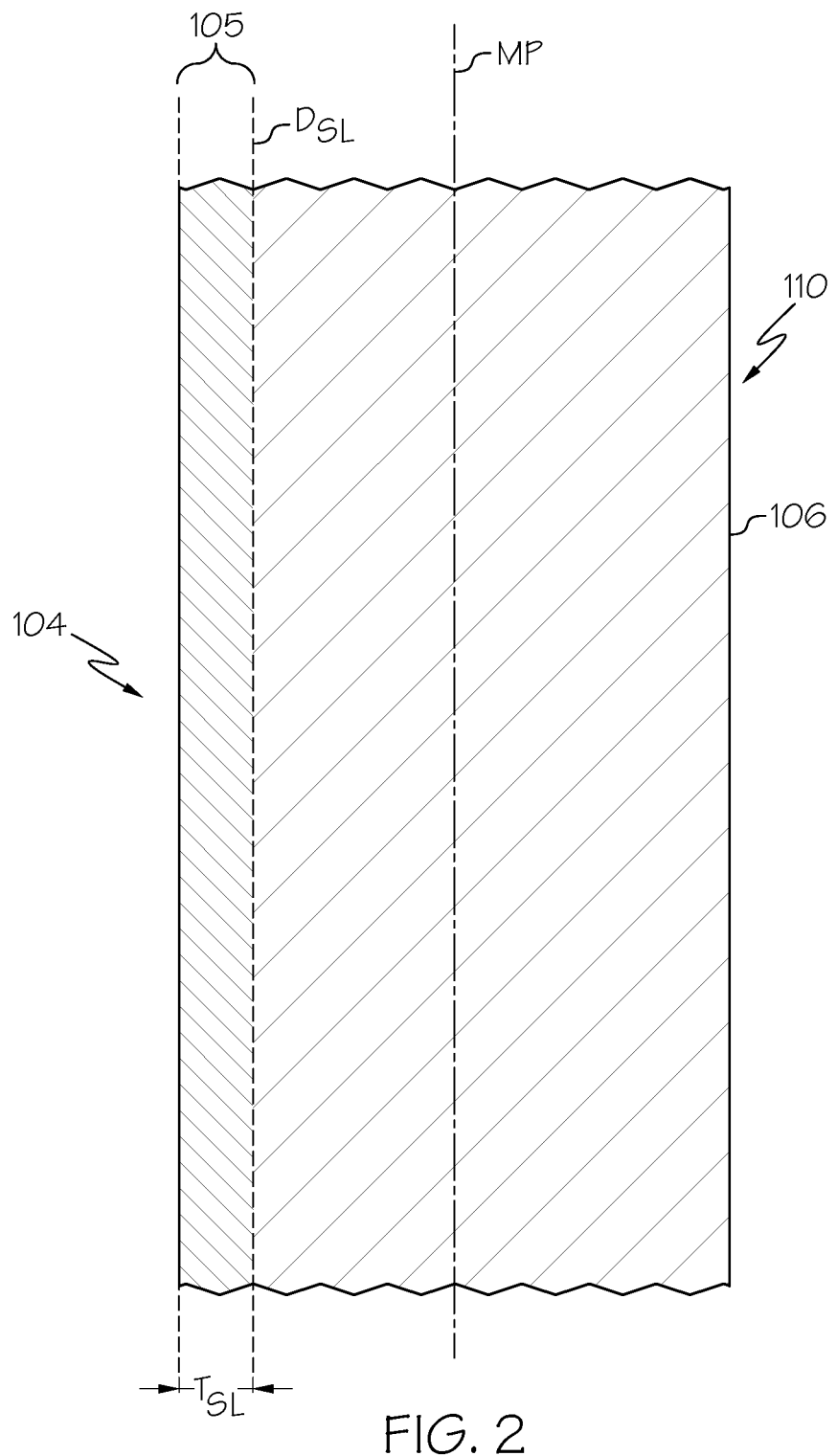
FIG. 2 schematically depicts a region of the sidewall of the glass container of FIG. 1 prior to removal of the interior surface layer according to one or more embodiments described herein.

Referring now to FIGS. 1 and 2, the embodiment shown in FIG. 2 schematically depicts the interior surface 104 of a region of a glass container 100, including the interior surface layer 105 which includes deposited volatilized species. The composition of the interior surface layer 105 is different than the composition of the glass deeper in the wall region, such as at the midpoint MP of the wall region 110. Specifically, FIG. 2 schematically depicts a partial cross section of a wall region 110 of the glass container 100 of FIG. 1. The glass body 102 of the glass container 100 includes an interior surface layer 105 which extends from the interior surface 104 of the glass container 100 into the thickness of the wall region 110 to a depth $D_{SL}$ from the interior surface 104 of the glass container. The glass composition within the interior surface layer 105 has a persistent layer heterogeneity relative to the glass at the midpoint MP of the wall region and, as such, it should be understood that the composition of the glass in the interior surface layer 105 is different than the glass at the midpoint MP of the wall region 110. In some embodiments, the thickness $T_{SL}$ of the interior surface layer is at least 30 nm. In some embodiments, the thickness $T_{SL}$ of the interior surface layer is at least 50 nm. In some embodiments, the thickness $T_{SL}$ of the interior surface layer is at least 100 nm. In some embodiments, the thickness $T_{SL}$ of the interior surface layer is at least 150 nm. In some other embodiments, the thickness $T_{SL}$ of the interior surface layer is at least 200 nm or even about 250 nm. In some other embodiments, the thickness $T_{SL}$ of the interior surface layer is at least 300 nm or even about 350 nm. In yet other embodiments, the thickness $T_{SL}$ of the interior surface layer is at least 500 nm. In some embodiments, the interior surface layer may extend to a thickness $T_{SL}$ of at least 1 µm or even at least 2 µm.

In the embodiments described herein, the phrase "persistent layer heterogeneity" means that the concentration of the constituent components (e.g., $SiO_2$, $Al_2O_3$, $Na_2O$, etc.) of the glass composition in the interior surface layer 105 vary from the concentration of the same constituent components at the midpoint of a thickness of the glass body (i.e., at a point along the midpoint line MP which evenly bisects the glass body between the interior surface 104 and the exterior surface 106) by an amount which would result in delamination of the glass body upon long term exposure to a solution contained within the glass container. In the embodiments described herein, the persistent layer heterogeneity in the interior surface layer of the glass body is such that an extrema (i.e., the minimum or maximum) of a layer concentration of each of the constituent components of the glass composition in the interior surface layer 105 is less than 92% or greater than 108% of the same constituent component at a midpoint of a thickness of the glass body when the glass container 100 is in an as received condition. In other embodiments, the persistent layer heterogeneity in the interior surface layer 105 of the glass body is such that the extrema of the layer concentration of each of the constituent components of the glass composition in the interior surface layer 105 is less than 90% or greater than 110% of the same constituent component at the midpoint of the thickness of the glass body when the glass container 100 is in an as received condition. In still other embodiments, the persistent layer heterogeneity in the interior surface layer 105 of the glass body is such that the extrema of the layer concentration of each of the constituent components of the glass composition in the interior surface layer 105 is less than 80% or greater than 120% of the same constituent component at the midpoint of the thickness of the glass body when the glass container 100 is in an as received condition. In some embodiments, the persistent layer heterogeneity is exclusive of constituent components of the glass composition which are present in an amount less than 2 mol. %. The persistent layer heterogeneity is also exclusive of any water which may be present in the glass composition.

In the embodiments described herein, the phrase "persistent layer homogeneity" means that the concentration of the constituent components (e.g., $SiO_2$, $Al_2O_3$, $Na_2O$, etc.) of the glass composition in the interior region do not vary from the concentration of the same constituent components at the midpoint of a thickness of the glass body (i.e., at a point along the midpoint line MP which evenly bisects the glass body between the modified interior surface 104 and the exterior surface 106) by an amount which would result in delamination of the glass body upon long term exposure to a solution contained within the glass container. In the embodiments described herein, the persistent layer homogeneity in the interior region of the glass body is such that an extrema (i.e., the minimum or maximum) of a layer concentration of each of the constituent components of the glass composition in the interior region 120 is greater than or equal to 80% and less than or equal to 120% of the same constituent component at a midpoint of a thickness of the glass body after the interior surface layer with the persistent layer heterogeneity has been removed from the glass container. In other embodiments, the persistent layer homogeneity in the interior region of the glass body is such that the extrema of the layer concentration of each of the constituent components of the glass composition in the interior region 120 is greater than or equal to 90% and less than or equal to 110% of the same constituent component at the midpoint of the thickness of the glass body after the interior surface layer with the persistent layer heterogeneity has been removed from the glass container. In still other embodiments, the persistent layer homogeneity in the interior region of the glass body is such that the extrema of the layer concentration of each of the constituent components of the glass composition in the interior region 120 is greater than or equal to 92% and less than or equal to 108% of the same constituent component at the midpoint of the thickness of the glass body after the interior surface layer with the persistent layer heterogeneity has been removed from the glass container. In some embodiments, the persistent layer homogeneity is exclusive of constituent components of the glass composition which are present in an amount less than 2 mol. %. The persistent layer homogeneity is also exclusive of any water which may be present in the glass composition.

The term "as received condition," as used herein, refers to the composition of the glass container 100 in an off the shelf condition with any coatings or treatments that are customarily included in a finished, commercial product. Coatings that may be included on glass containers in the "as received condition" may include lubricous and thermal coatings or barrier coating like PECVD silicone dioxide. Treatments that the "as received condition" containers may undergo include chemical or thermal strengthening, annealing, or the like. One exception to the "as received condition" is sulfate or fluoride treated glass containers. As will be discussed in more detail below, the CDR of treated glass containers is, in embodiments, measured before the treatment is conducted.

If an interior surface layer 105 of deposited volatilized species remains on the interior surface 104 or is reincorporated during an annealing process, solutions contained in the container may leach the deposited volatilized species from the interior surface layer 105. As these volatilized species are leached from the glass, a high silica glass network (gel) remains on the interior surface 104 which swells and strains during hydration and eventually spalls from the surface (i.e., the interior surface 104 of the glass container 100 delaminates), potentially introducing particulate matter into the solution contained within the glass container. In embodiments where the glass container is a vial, such as depicted in FIG. 1, forming the neck of the vial may cause volatilization of borate species and alkali species, such as, for example, sodium. These volatilized borate species and alkali species may then be re-deposited on the wall region 110, the shoulder region 116, the base region 112, and the heel region 114 and the lower sidewall (region of 110 near 114) of the glass container 100. Thus, in such embodiments, the lower sidewall region and the heel region 114 of the glass container 100 comprise higher amounts of borate species and alkali species than the wall region 110 of the glass container 100. Once the glass container 100 is filled with a solution, such as, for example, a pharmaceutical compound, the borate species and the alkali species may be dissolved into the pharmaceutical compound leaving the surface of the heel region 114 with high concentrations of silica, such as silica gel, relative to the wall region 110. This surface layer with high concentrations of silica may, over time, swell due to the continued reaction with the pharmaceutical and buckle from the induced stress causing delamination of material from the lower sidewall region and the heel region 114 of the glass container 100. In fact, this delamination is so prevalent that on Mar. 24, 2011 the U.S. Food and Drug Administration issued an advisory notifying manufacturers of the possible formation of glass lamellae in small-volume glass vials.

As noted above, delamination may result in the release of silica-rich glass flakes, or lamellae, into a solution contained within the glass container after extended exposure to the solution. And, due to volatilization of certain species, such as borates and alkali, the base region and the heel region of a glass container are the most likely regions of the glass container to have silica-rich layers. Accordingly, the risk of the glass container to delaminate is highest at the lower sidewall region and the heel region of the glass container. However, conventional methods for determining the chemical heterogeneity of glass containers are not narrowly tailored or focused to produce reliable results based on the above concerns.

Conventional methods for interrogating chemical heterogeneity of glass articles include USP <660> testing, methylene blue testing, USP <1660> testing, and Schott Quicktest, which is described in U.S. Pat. No. 9,322,766. However, each of these testing methodologies has drawbacks, as described herein below.

USP <660> Surface Glass Test requires that the glass containers be filled to 90% capacity with treatment fluid, thus it averages the results over the full interior surface area of the glass and does not focus on the heel and lower sidewall of the glass container, which has higher risk for delamination. For instance, high chemical heterogeneity in the heel region will be diluted by the 90% fill. Further, the amount of fluid used for each container is nearly the entire quantity of the glass container. In addition, the USP <660> Surface Glass Test results can mask the presence of ammonium sulfates or surface coatings. Thus, USP <660> Surface Glass Test does not specifically target the regions of the glass container that are likely to delaminate, preventing the detection of deposited material that may have been generated during the conversion process. USP <660> Surface Glass Test is not a reliable test for determining the chemical heterogeneity of glass containers.

Methylene blue testing is conventionally used to indicate, by staining, areas where certain chemical components are present. However, methylene blue does reliably not stain regions of the glass that have a high risk for delamination, and methylene blue does not provide quantitative results. Further, methylene blue is prone to providing false positives. Thus, methylene blue is not a reliable test for determining the chemical heterogeneity of glass containers.

USP <1660> testing recommends heating at elevated temperatures. These elevated temperatures may cause dissolution of the flakes, or lamellae, in the test solution, which leads to unreliable results. Also, the swelling and dislodgement of the silica-rich layer takes extended periods of time that are not always reproducible with accelerated testing procedures. In addition, the accelerated testing procedures can activate chemical mechanisms that either do not occur in the usable lifetime of the glass container, or are different chemical mechanisms than those that actually occur. Thus, the accelerated testing procedures of USP <1660> can result in unreliable testing results. Finally, USP <1660> does not provide for a positive control. The accelerated testing procedures and test solutions used in USP <1660> do not provide for comparison of the test population with a positive control lot of glass containers that has proven delamination risk. Thus, USP <1660> is not a reliable test for determining the chemical heterogeneity of glass containers.

The Schott Quicktest does not account for all chemical heterogeneity in the glass container. Thus, glass containers that pass the Schott Quicktest may still have chemical heterogeneity on their glass surfaces that can result in delamination. In particular, the Schott Quicktest only measures the amount of sodium deposition on the surface of the glass; it does not account for the volatilization and deposition of borate species. The Schott Quicktest also does not account for the effect that annealing has on the glass container, which results in the reincorporation of deposited material from the glass surface into the glass network. Thus, the Schott Quicktest is not a reliable test for determining the chemical heterogeneity of glass containers.

In view of the above deficiencies in conventional tests, embodiments disclosed herein provide methods for determining the chemical heterogeneity of glass containers, and some embodiments particularly provide methods for determining the chemical heterogeneity of the regions of glass containers that have a high risk for delaminating as a result of their chemical heterogeneity. By focusing the testing on the region of the glass container having a high risk for delamination, accurate results can be achieved without the need to fill the glass containers to the 90% fill rate required by USP <660>. Accordingly, in embodiments, multiple glass containers may be tested simultaneously with very little solvent and yielding highly accurate results.

In embodiments disclosed herein, the chemical heterogeneity of a glass container may be measured by calculating the Chemical Durability Ratio (CDR) of the glass container. The CDR of the glass container is a ratio of the titrant volume of an as received glass container to the titrant volume of an etched glass container. As used herein, the term "as received glass container" refers to an off the shelf condition container with any coatings or treatments that are customarily included in a finished, commercial product. However, one exception to the "as received glass container" are sulfate or fluoride treated glass containers. As will be discussed in more detail below, the CDR of sulfate-treated or fluoride glass containers is, in embodiments, measured before the sulfate or fluoride treatment is conducted. Coatings that may be included on glass containers in the "as received glass container" may include lubricous and thermal coatings or barrier coating like PECVD silicone dioxide. Treatments that the "as received glass container" may undergo include chemical or thermal strengthening, annealing, or the like. The CDR of a glass container may be calculated using the following formula (1):

$$CDR = \frac{\text{As Received Titrant Volume}}{\text{Etched Titrant Volume}} \quad (1)$$

By calculating the CDR of a glass container using the above Equation (1), the chemical heterogeneity of the glass container may be determined. Namely, a glass container having a CDR near unity (i.e., CDR≈1) has minimal chemical heterogeneity and will, therefore, have little to no delamination risk. Likewise, a glass container having a CDR that deviates greatly from unity—having a CDR much greater or much less than 1—has chemical heterogeneity and will, therefore, have a higher risk for delamination. In embodiments, glass containers having a CDR from greater than or equal to 0.6 to less than or equal to 1.6, such as from greater than or equal to 0.7 to less than or equal to 1.5 may be considered to have minimal chemical heterogeneity and will not be likely to delaminate. In other embodiments, glass containers having a CDR from greater than or equal to 0.8 to less than or equal to 1.2, such as from greater than or equal to 0.9 to less than or equal to 1.1 may be considered to have no chemical heterogeneity and will not be likely to delaminate. As the CDR deviates from the desired range, the risk for delamination increases.

In one or more embodiments, glass containers are not likely to delaminate if the CDR value is less than 6.0, such as less than or equal to 5.5, less than or equal to 5.0, less than or equal to 4.5, less than or equal to 4.0, less than or equal to 3.5, less than or equal to 3.0, less than or equal to 2.5, less than or equal to 2.0, or less than or equal to 1.5. As described above, the closer the CDR value is to unity (i.e., a CDR≈1.0), the less likely delamination is to occur. Accordingly, even though a CDR value of less than 6.0 indicates that delamination is not likely, a glass container having a CDR value of, for example, 3.0 is less likely to delaminate than a glass container having a CDR value higher than 3.0, such as, for example, a glass container having a CDR value of 4.0. Therefore, it should also be understood that the CDR test measures the likelihood that delamination will occur in a glass container. Accordingly, although glass containers with a CDR value less than 6.0 have a low propensity for delamination, having a CDR value less than 6.0 is not a guarantee that the glass container will not delaminate in any condition (such as at long storage times and with caustic container contents). As the CDR value increases from 1.0, the likelihood of delamination also increases. Thus, even glass containers with a CDR value of 2.0 have a greater risk for delamination than glass containers with a CDR value of 1.0. So, in certain situations where delamination of the glass container may cause little harm, a glass container with a CDR value of, for example, 2.0 may be sufficient. But, in situations where delamination can cause great harm, a glass container with a CDR value of about 1.0 may be required.

Embodiments of methods for obtaining the as received titrant volume and the etched titrant volume will now be described. A plurality of glass containers are used, and each glass container of the plurality may have similar compositions, geometries and capacity as the other glass containers of the plurality. As used herein, "similar compositions, geometries and capacities" means that each glass container has the same composition, has the same capacity, and has the same shape taking into consideration reasonable manufacturing tolerances. Initially, the glass containers are rinsed at least three times with high purity water to remove any environmental contaminants that may be present on the interior surface of the glass containers. As used herein, "high purity water" refers to water having at least 10 MΩ-cm, such as purified water defined by USP <1231>, freshly distilled water, water consistent with current EP purified water [EP Chapter 4.1.1—water], water R or R1, or USP carbon dioxide-free water. After the glass containers are rinsed with the high purity water, they are emptied and the high purity water is discarded and the containers are completely emptied and tap dried, such as by repeatedly taping the container against a soft surface until no additional high purity water is released from the glass container.

Once the glass containers have been rinsed, the amount of solvent needed to determine the chemical heterogeneity of the glass container is calculated. As disclosed above, the heel region of a glass container has a high risk for delamination caused by chemical heterogeneity. Thus, the delamination risk of a glass container can be assessed by filling a glass container with enough solvent to cover the heterogeneous region of the glass container (such as the heel and slightly above the heel). In embodiments, this can be achieved by filling the glass container with solvent such that the solvent comprises from greater than or equal to 5.0% by volume of the glass container to less than or equal to 50.0% by volume of the glass container, such as from greater than or equal to 6.0% by volume of the glass container to less than or equal to 35.0% by volume of the glass container, from greater than or equal to 8.0% by volume of the glass container to less than or equal to 25.0% by volume of the glass container, from greater than or equal to 9.0% by volume of the glass container to less than or equal to 15.0% by volume of the glass container, or even from greater than or equal to 10.0% by volume of the glass container to less than or equal to 14.0% by volume of the glass container. In other embodiments, the glass container may be filled with solvent such that the solvent comprises from greater than or equal to 11.0% by volume of the glass container to less than or equal to 13.0% by volume of the glass container, such as about 12.5% by volume of the glass container. The amount of solvent that is required to fill the glass container to the required percentage is calculated by filling at least 6 glass containers to brimful capacity and averaging the brimful capacity of the at least 6 glass containers. This average brimful capacity can then be used to calculate the volume of solvent that will be added to the glass container to correspond to the desired percentage. As an example, and without limitation, if the average brimful capacity of the at least 6 glass containers is 10.0 mL, and the desired percentage is 12.5% by volume, the actual volume at which the glass containers are filled with solvent is 1.25 mL, with measurement precision of at least 0.1 mL. In embodiments, the solvent is high purity water. In other embodiments, the solvent may be an acid, a base, or a glycine solution.

In embodiments, the total number of glass containers to be tested will be determined based upon the actual volume of solvent that is added to the glass containers and the volume of solution needed to perform the titration. In some embodiments, the titration will require greater than or equal to 25 mL of solution, such as greater than or equal to 40 mL of solution, or even greater than or equal to 45 mL of solution. In some embodiments, the titration will require greater than or equal to 50 mL of solution, such as greater than or equal to 60 mL of solution, or even greater than or equal to 100 mL of solution. It should be understood that excess solution (i.e., more than the amount of solution needed to perform the titration) may be formed, and then the amount of solution needed to run the titration can be separated from the excess solution. The excess solution may then be used for other tests. For small containers with high normalized titration values, 25 mL can be used, and only 1 replicate is needed. However, as the container capacity increases and the titrant volume decreases, the pooled volume increases to 50 mL and the replicates increase to 2 and 3. For vials of >100 mL brimful capacity, the test requires 100 mL of solution from at least 3 containers to be titrated with 3 replicate titrations. So, to calculate the number of containers needed: [(Pooled Volume to titrate—25, 50, or 100 mL)/0.125*(brimful volume)]=number of vials per replicate. This number should be greater than 3 and is generally increased by 5-10% to account for evaporation loss during autoclave. Total vials needed=number of vials per replicate*(number of replicates). In embodiments the number of glass containers that may be tested is from greater than or equal to 10 glass containers to less than or equal to 300 glass containers, such as from greater than or equal to 100 glass containers to less than or equal to 250 glass containers, or even from greater than or equal to 120 glass containers to less than or equal to 220 glass containers. It should be understood that this number will vary depending on the size of the containers being tested.

The number of glass containers to be tested, as determined by the foregoing calculation, are filled with solvent to the desired percentage and covered with cleaned ultra-high vacuum aluminum foil or a leached glass article, such as, for example, a petri dish. Once covered, the glass containers are heated to a temperature from greater than or equal to 90° C. to less than or equal to 130° C., such as from greater than or equal to 95° C. to less than or equal to 125° C. According to some embodiments, the heating includes placing the covered glass containers into an autoclave containing water at ambient temperature. The covered glass containers may be held above the level of the water in the autoclave to ensure that they are not contaminated by the water in the autoclave. Once the autoclave is loaded with the glass containers, it is heated to about 100° C. and steam is permitted to issue from the vent cock for about 10 minutes. After the about 10 minutes has elapsed, the vent cock is closed and the autoclave is heated from about 100° C. to about 121° C. at a rate of about 1° C. per minute. The autoclave temperature is maintained at 121±1° C. for 60±1 minutes. Subsequently, the temperature of the autoclave is lowered from about 121° C. to about 100° C. at a rate of about 0.5° C. per minute with venting to prevent a vacuum from forming within the autoclave. The autoclave is allowed to then cool to about 95° C. before it is opened and the glass containers are removed from the autoclave. The glass containers can then be cooled in a water bath at about 80° C. that is replenished with cold running tap water. In some embodiments, a cooling plate and fans are used in place of the water bath. Regardless of whether a water bath or cooling plate is used to cool the glass containers, the glass containers should be cooled for less than or equal to 30 minutes, such as less than or equal to 25 minutes, less than or equal to 20 minutes, or even less than or equal to 10 minutes. After cooling, the temperature of the solution in the glass containers should be less than or equal to 25° C., such as less than or equal to 23° C.

In embodiments, in less than or equal to one hour after the glass containers have been removed from the autoclave, the solution is titrated. To titrate the solution, the solution from each of the glass containers is consolidated into a single vessel using a pre-cleaned funnel. The volume of the consolidated solution should be greater than or equal to the amount required for titration. The correct volume (25, 50, or 100 mL) of consolidated solution is measured and placed into a pre-leached vessel suitable for conducting the titration. Once consolidated, according to embodiments, the appropriate amount of the consolidated solution needed for the titration is collected and methyl red indicator is added. In embodiments, about 0.05 mL of methyl red indicator is added per 25 mL of solution.

A titration blank is formulated having substantially the same volume as the consolidated solution from the glass containers, and is formulated from high purity water with the addition of 0.05 mL of methyl red per 25 mL of high purity water.

In embodiments, the titration blank is titrated by adding 0.01 M HCl to the titration blank in a drop-wise manner. The volume of HCl required to change the color of the titration blank is recorded and should be below 0.1 mL per 100 mL of consolidated solution. The consolidated solution from the glass containers is similarly titrated by adding 0.01 M HCl to the consolidated solution in a drop-wise manner. The volume of the HCl required to change the color of the consolidated solution is recorded. It should be understood that the consolidated solution and the blank may be titrated in any order. In some embodiments, the volume of HCl required to change the color of the titration blank is subtracted from the volume of the HCl required to change the color of the consolidated solution. The results of the titration are recorded in mL of 0.01 M HCl per 100 mL of the consolidated solution. This result is the as received titrant volume.

Embodiments of methods for determining the etched titrant volume will now be disclosed. The methods for determining the etched titrant volume are similar to the methods described above for the as received titrant volume; however, to determine the etched titrant volume, a thin layer of the interior surface of the glass container is removed by etching. The etching may take place on the interior surface of the glass container or on the interior and exterior surfaces of the glass container.

According to embodiments, suitable etchants for removing the layer of the interior surface of the glass container are mixtures of HCl and HF. Suitable etchants are disclosed, for example, in U.S. Patent Application Publication No. 2016/0145150, which is incorporated herein in its entirety. In embodiments, the etchant is a trace metal grade etchant, such as HCl A1445-212 manufactured by Fisher Scientific and HF 9560-06 manufactured by JT Baker or as disclosed in U.S. Pat. No. 9,346,707, which is incorporated herein by reference in its entirety. In some embodiments, the etchant may comprise HF at a concentration from greater than or equal to 1.0 M to less than or equal to 3.0 M, such as from greater than or equal to 1.5 M to less than or equal to 2.5 M, such as about 2.0 M. In embodiments, the etchant may comprise HCl at a concentration from greater than or equal to 2.0 M to less than or equal to 4.0 M, such as from greater than or equal to 2.5 M to less than or equal to 3.5 M, such as about 3.0 M. It should be understood that the concentration of both HF and HCl may be selected to achieve the desired etch rate for a particular glass composition that is being etched. It should be understood that in one or more embodiments other inorganic acids, such as, for example, $H_2SO_4$, $HNO_3$, $H_3PO_4$, $H_3BO_3$, and HBr, may be used in place of, or in addition to, HF and/or HCl.

As noted above, the concentration of HF and HCl in the etchant is selected to so that the etchant etches the glass container at a desired etch rate. The desired etch rate is selected to etch a layer of the interior surface of the glass container that has a thickness from greater than or equal to 0.75 μm to less than or equal to 15 μm for a duration from greater than or equal to 1 minute to less than or equal to 60 minutes. In embodiments, the thickness of the layer of the interior surface of the glass container that is removed is from greater than or equal to 0.75 μm to less than or equal to 5 μm, such as from greater than or equal to 0.85 μm to less than or equal to 1.5 μm, or even from greater than or equal to 0.95 μm to less than or equal to 1.25 μm. In embodiments, the thickness of the layer of the interior surface of the glass container that is removed is at least 1.00 μm. In embodiments, the duration of the etching process is from greater than or equal to 1.0 minute to less than or equal to 60 minutes, such as from greater than or equal to 2.0 minutes to less than or equal to 4.0 minutes. In other embodiments, the duration of the etching process is from greater than or equal to 2.5 minutes to less than or equal to 3.5 minutes, such as about 3.0 minutes. Without being bound to any particular theory, it is believed that volatilized constituents are deposited and reincorporated on the glass container at depths up to about 500 nm. Therefore, removing more than 500 nm by etching is desired so that the titrant contacts the region of the glass container having the bulk concentration (i.e., the concentration without volatilized and deposited components). It should be understood that the etching can be conducted by placing etchant in the interior of the glass container or by submerging the glass container in an etchant bath. The thickness may be determined, in embodiments, by the following equation: thickness=mass/density/surface area etched.

According to embodiments, once the glass containers have been etched, they are soaked in a room temperature water bath for about 5 minutes. After the 5 minute soak time is complete, the glass containers are soaked in a second water bath for about 5 minutes. This process can be repeated any number of times to remove residual etchant from the glass containers. After all the soaking steps are complete, the glass containers are, according to some embodiments, washed approximately six times with water having a conductivity of 18 MΩ-cm or more, such as purified water defined by USP <1231>, freshly distilled water, water consistent with current EP purified water [EP Chapter 4.1.1—water], water R or R1, or USP carbon dioxide-free water. In some embodiments, the glass containers are washed three times in 16 MΩ-cm water, and subsequently, the containers are washed at least three times in 18 MΩ-cm water to ensure that the etched surfaces of the glass containers are free from contaminants.

Once the glass containers have been etched and cleaned, the amount of solvent needed to determine the chemical heterogeneity of the glass container is calculated. According to embodiments, roughly the same amount of solvent should be added to the etched glass containers as the amount of solvent that was added to the as received glass containers so that roughly the same regions of the glass containers are being measured by the titration after etching. In embodiments, this can be achieved by filling the etched glass containers with solvent such that the solvent comprises from greater than or equal to 5.0% by volume of the glass container to less than or equal to 50.0% by volume of the glass container, such as from greater than or equal to 6.0% by volume of the glass container to less than or equal to 35.0% by volume of the glass container, from greater than or equal to 8.0% by volume of the glass container to less than or equal to 25.0% by volume of the glass container, from greater than or equal to 9.0% by volume of the glass container to less than or equal to 15% by volume of the glass container, or even from greater than or equal to 10.0% by volume of the glass container to less than or equal to 14.0% by volume of the glass container. In other embodiments, the etched glass containers may be filled with solvent such that the solvent comprises from greater than or equal to 11.0% by volume of the glass container to less than or equal to 13.0% by volume of the glass container, such as about 12.5% by volume of the glass container. The amount of solvent that is required to fill the etched glass container to the required percentage is calculated by filling at least 6 etched glass containers to brimful capacity and averaging the brimful capacity of the at least 6 etched glass containers. This average brimful capacity can then be used to calculate the actual volume of solvent that will be added to the glass container to correspond to the desired percentage. In embodiments, the solvent is high purity water. In some embodiments, the solvent may be an acid, a base, or a glycine solution.

In embodiments, the total number of etched glass containers to be tested will be determined based upon the actual volume of solvent that is added to the glass containers and the volume of solution needed to perform the titration. In some embodiments, the titration will require greater than or equal to 25 mL of solution, such as greater than or equal to 40 mL of solution, or even greater than or equal to 45 mL of solution. In some embodiments, the titration will require greater than or equal to 50 mL of solution, such as greater than or equal to 60 mL of solution, or even greater than or equal to 100 mL of solution. It should be understood that excess solution (i.e., more than the amount of solution needed to perform the titration) may be formed, and then the amount of solution needed to run the titration can be separated from the excess solution. The number of etched glass containers to be tested can be determined as defined above. In embodiments the number of glass containers that may be tested is from greater than or equal to 10 glass containers to less than or equal to 300 glass containers, such as from greater than or equal to 100 glass containers to less than or equal to 250 glass containers, or even from greater than or equal to 120 glass containers to less than or equal to 220 glass containers. It should be understood that the number of containers will vary depending on the capacity of the containers being tested.

The number of etched glass containers to be tested, as determined by the foregoing calculation, are filled with the desired percentage of solvent and covered with cleaned ultra-high vacuum aluminum foil or a leached glass article, such as, for example, a petri dish. Once covered, the glass containers are heated to a temperature from greater than or equal to 90° C. to less than or equal to 130° C., such as from greater than or equal to 95° C. to less than or equal to 125° C. In some embodiments, the heating includes placing the etched glass containers into an autoclave containing water at ambient temperature. The covered, etched glass containers may be held above the level of the water in the autoclave to ensure that they are not contaminated by the water in the autoclave. Once the autoclave is loaded with the etched glass containers, it is heated to about 100° C. and steam is permitted to issue from the vent cock for about 10 minutes. After the about 10 minutes has elapsed, the vent cock is closed and the autoclave is heated from about 100° C. to about 121° C. at a rate of about 1° C. per minute. The autoclave temperature is maintained at 121±1° C. for 60±1 minutes. Subsequently, the temperature of the autoclave is lowered from about 121° C. to about 100° C. at a rate of about 0.5° C. per minute with venting to prevent a vacuum from forming within the autoclave. The autoclave is allowed to then cool to about 95° C. before it is opened and the glass containers are removed from the autoclave. The glass containers can then be cooled in a water bath at about 80° C. that is replenished with cold running tap water. In some embodiments, a cooling plate and fans are used in place of the water bath. Regardless of whether a water bath or cooling plate is used to cool the glass containers, the glass containers should be cooled for less than or equal to 30 minutes, such as less than or equal to 25 minutes, or even less than or equal to 20 minutes. After cooling, the temperature of the solution in the etched glass containers should be less than or equal to 25° C., such as less than or equal to 23° C.

In embodiments, in less than or equal to one hour after the etched glass containers have been removed from the autoclave, the solution is titrated. To titrate the solution, the solution from each of the etched glass containers is consolidated into a single vessel using a pre-cleaned funnel. As discussed above, the volume of the consolidated amount of solution should be greater than or equal to the amount required to titrate the solution. Once consolidated, according to embodiments, the amount of the consolidated solution needed to conduct the titration is extracted and red indicator is added. In embodiments, about 0.05 mL of methyl red indicator is added per 25 mL of solution.

A titration blank is formulated having substantially the same volume as the consolidated solution from the glass containers. The volume of the titration blank is substantially the same as the volume required for titrating the solution, and is formulated from high purity water, such as purified water defined by USP <1231>, freshly distilled water, water consistent with current EP purified water [EP Chapter 4.1.1—water], water R or R1, or USP carbon dioxide-free water, with the addition of 0.05 mL of methyl red per 25 mL of high purity water.

In embodiments, the titration blank is titrated by adding 0.01 M HCl to the titration blank in a drop-wise manner. The volume of HCl required to change the color of the titration blank is recorded. The consolidated solution from the etched glass containers is titrated by adding 0.01 M HCl to the consolidated solution in a drop-wise manner. The volume of the HCl required to change the color of the consolidated solution is recorded. In some embodiments, the volume of HCl required to change the color of the titration blank is subtracted from the volume of the HCl required to change the color of the consolidated solution. The results of the titration are recorded in mL of 0.01 M HCl per 100 mL of the consolidated solution. This result is the etched titrant volume.

It should be understood that the above titration processes—both for the as received glass containers and the etched glass containers—can be automated by using a calibrated automated titration device. Such devices are well known in the art and include, as an example, a Metrohm with an 888 Titrando exchange unit (operational Apr. 25, 2014) containing an 814 USB Sample processor autosampler. The automated titration device parameters may be set as follows: 5 mL/min dosing rate; 60 second pause between additions; 0.02 mL dosing volume increase; and 25 mV/min signal drift.

Once measured, the as received titrant volume and the etched titrant volume can then be used in Equation (1) to obtain the CDR value, which represents the durability of the heel region and the base region of the glass container. As outlined above, a CDR value near unity indicates that little to no chemical heterogeneity exists in the heel region and the base region of the glass container, thus the glass container will have little to no delamination. However, the further the CDR value is from unity, the risk of delamination increases.

As noted above, one exception to the "as received condition" is glass containers that have been sulfate treated. It has been found that some glass containers that have been sulfate treated will delaminate even though the CDR value for some sulfate-treated glass containers is around 1.0. Without being bound by any particular theory, it is believed that shallow surface layers of glass containers that have been sulfate treated have low amounts of borate because the sulfate treatment pulls borate species out of the shallow portion of the glass container surface. Accordingly, in such situations, the titrant volume of the as received container is low in borate and is similar to the titrant volume of the etched container, which yields a CDR value at or near 1.0. However, it has been shown that delamination can occur during storage of sulfate treated glass containers. It is believed that although the sulfate treatment pulls borate out of a shallow surface of the glass container, borate species are still present beyond that shallow surface into the thickness of a sidewall of the glass container. This borate-containing layer can cause delamination. Put differently, in sulfate treated glass containers, there is a shallow layer with low amounts of borate at the surface of the glass container, a middle layer with higher amounts of borate deeper into the thickness a sidewall of the glass container, and a bulk layer with low amounts of borate even deeper into the thickness of a sidewall of the glass container that is at or near the center thickness of the sidewall. In this situation, the as received titrant volume in the CDR test is measured at the shallow layer with low amounts of borate, and the etched titrant volume is measured at the bulk layer with low amounts of borate. This results in a CDR value at or near 1.0, but ignores the middle layer that has higher amounts of borate, which can cause delamination.

Thus, according to embodiments, sulfate treated glass containers are tested—as described herein in detail—before the sulfate treatment is conducted. When this is done, the as received titrant volume will not be effected by the sulfate treatment. Where a glass container has a CDR value that indicates that the glass container is not likely to delaminate (such as, for example, a CDR value less than 6.0) before a sulfate treatment is conducted, then the glass container may be treated with sulfate and delamination is not likely to occur. However, where a glass container has a CDR value that indicates that the glass container may delaminate (such as, for example, a CDR value greater than 6.0), before a sulfate treatment is conducted, then the glass container is likely to delaminate even after a sulfate treatment. Accordingly, only glass containers that have a CDR value before sulfate treatment that indicates the glass container does not have a propensity to delaminate (such as, for example, a CDR value less than 6.0) should be sulfate treated.

As described above, the heel region of a glass container has a high risk for delamination because volatilized species are prone to deposit on the heel region of the glass container. Referring again to FIG. 1, another area of the glass container that has a risk for delamination is a shoulder region 116 of the glass container 100. Therefore, in some embodiments, it may be desirable to measure the CDR of the shoulder region 116 to determine whether the shoulder region 116 has chemical heterogeneity and, thus, is prone to delamination, which is particularly prevalent in molded vials. Testing the shoulder region 116 of the glass container is conducted in a similar manner as testing the heel region 114 of the glass container, except that once the titrant is added to the glass container, the glass container is inverted to measure the CDR at the shoulder of the glass container. This inverted CDR test is described in more detail below.

A plurality of glass containers are used, and each glass container of the plurality may have similar geometries and capacities as the other glass containers of the plurality. Initially, the glass containers are rinsed at least three times with high purity water to remove any environmental contaminants that may be present on the interior surface of the glass containers. After the glass containers are rinsed with the high purity water, they are emptied and the high purity water is discarded.

Once the glass containers have been rinsed, the amount of solvent needed to determine the chemical heterogeneity of the glass container is calculated. As disclosed above, the shoulder region of a glass container has a risk for delamination caused by chemical heterogeneity. Thus, the delamination of some glass containers may be accurately determined by filling a glass container with enough solvent to cover the shoulder region and a portion of the vertical sidewall near shoulder region of the of the glass container when the glass container is in an inverted position. In embodiments, this can be achieved by filling the glass container with solvent such that the solvent comprises from greater than or equal to 5.0% by volume of the glass container to less than or equal to 50.0% by volume of the glass container, such as from greater than or equal to 6.0% by volume of the glass container to less than or equal to 35.0% by volume of the glass container, from greater than or equal to 8.0% by volume of the glass container to less than or equal to 25.0% by volume of the glass container, from greater than or equal to 9.0% by volume of the glass container to less than or equal to 15% by volume of the glass container, or even from greater than or equal to 10.0% by volume of the glass container to less than or equal to 14.0% by volume of the glass container. In other embodiments, the glass container may be filled with solvent such that the solvent comprises from greater than or equal to 11.0% by volume of the glass container to less than or equal to 13.0% by volume of the glass container, such as about 12.5% by volume of the glass container. The amount of solvent that is required to fill the glass container to the required percentage is calculated by filling at least 6 glass containers to brimful capacity and averaging the brimful capacity of the at least 6 glass containers. This average brimful capacity can then be used to calculate the actual volume of solvent that will be added to the glass container to correspond to the desired percentage. As an example, and without limitation, if the average brimful capacity of the at least 6 glass containers is 10 mL, and the desired percentage is 12.5% by volume, the actual volume at which containers to be tested will be filled with solvent is 1.25 mL. In embodiments, the solvent is high purity water.

In embodiments, the total number of glass containers to be tested will be determined based upon the actual volume of solvent that is added to the glass containers and the volume of solution needed to perform the titration. In some embodiments, the titration will require greater than or equal to 25 mL of solution, such as greater than or equal to 40 mL of solution, or even greater than or equal to 45 mL of solution. In some embodiments, the titration will require greater than or equal to 50 mL of solution, such as greater than or equal to 60 mL of solution, or even greater than or equal to 100 mL of solution. It should be understood that excess solution (i.e., more than the amount of solution needed to perform the titration) may be formed, and then the amount of solution needed to run the titration can be separated from the excess solution. The excess solution can then be used for additional testing. The number of glass containers to be tested can be determined as described above. In embodiments the number of glass containers that may be tested is from greater than or equal to 10 glass containers to less than or equal to 300 glass containers, such as from greater than or equal to 100 glass containers to less than or equal to 250 glass containers, or even from greater than or equal to 120 glass containers to less than or equal to 220 glass containers. It should be understood that the number of containers will vary depending on the capacity of the containers to be tested.

The number of glass containers to be tested, as determined by the foregoing calculation, are filled with the desired percentage of solvent and covered with a water tight plug. According to embodiments, the water tight plug should be constructed of a material that has little to no effect on the titration results of the glass container. In some embodiments, a deviation of the as received titrant volume caused by the water tight plug may be less than or equal to 0.20 mL per 100 mL of solution, such as less than or equal to 0.15 mL per 100 mL of solution, or even less than or equal to 0.10 mL per 100 mL of solution. In some embodiments, the water tight plug may be a Teflon™ coated rubber or plastic plug. The plug should be pre-leached prior to use by exposure to water in an autoclave cycle. Other embodiments could include a plug that is covered with Teflon tape or a PTFE septum.

The plugged glass containers are then inverted so that the solution is in contact with the shoulder region of the glass container. The glass containers are heated to a temperature from greater than or equal to 90° C. to less than or equal to 130° C., such as from greater than or equal to 95° C. to less than or equal to 125° C. In some embodiments, the heating includes placing the glass containers into an autoclave containing water at ambient temperature. Once the autoclave is loaded with the plugged glass containers, it is heated to about 100° C. and steam is permitted to issue from the vent cock for about 10 minutes. After the about 10 minutes has elapsed, the vent cock is closed and the autoclave is heated from about 100° C. to about 121° C. at a rate of about 1° C. per minute. The autoclave temperature is maintained at 121±1° C. for 60±1 minutes. Subsequently, the temperature of the autoclave is lowered from about 121° C. to about 100° C. at a rate of about 0.5° C. per minute with venting to prevent a vacuum from forming within the autoclave. The autoclave is allowed to then cool to about 95° C. before it is opened and the plugged glass containers are removed from the autoclave, while maintaining their inverted position. The inverted, plugged glass containers can then be cooled in a water bath at about 80° C. that is replenished with cold running tap water. In some embodiments, a cooling plate and fans are used in place of the water bath. Regardless of whether a water bath or cooling plate is used to cool the plugged glass containers, the plugged glass containers should be cooled for less than or equal to 30 minutes, such as less than or equal to 25 minutes, less than or equal to 20 minutes, or even less than 10 minutes. The plugged glass containers are maintained in there inverted position throughout the cooling process. After cooling, the temperature of the solution in the plugged glass containers should be less than or equal to 25° C., such as less than or equal to 23° C.

In embodiments, in less than or equal to one hour after the inverted, plugged glass containers have been removed from the autoclave, the solution is titrated. To titrate the solution, the glass containers are unplugged and the solution from each of the glass containers is consolidated into a single vessel using a pre-cleaned funnel. The volume of the consolidated amount of solution should be greater than or equal to the amount required to titrate the solution. Once consolidated, according to embodiments, the amount of solution needed to complete the titration is extracted from the consolidated solution and methyl red indicator is added. In embodiments, about 0.05 mL of methyl red indicator is added per 25 mL of solution.

A titration blank is formulated having substantially the same volume as the consolidated solution from the glass containers. The volume of the titration blank is substantially the same as the volume required for titrating the solution, and is formulated from high purity water with the addition of 0.05 mL of methyl red per 25 mL of high purity water.

In embodiments, the titration blank is titrated by adding 0.01 M HCl to the titration blank in a drop-wise manner. The volume of HCl required to change the color of the titration blank is recorded. The consolidated solution from the glass containers is titrated by adding 0.01 M HCl to the consolidated solution in a drop-wise manner. The volume of the HCl required to change the color of the consolidated solution is recorded. In some embodiments, the volume of HCl required to change the color of the titration blank is subtracted from the volume of the HCl required to change the color of the consolidated solution. The results of the titration are recorded in mL of 0.01 M HCl per 100 mL of the consolidated solution. This result is the as received titrant volume.

Embodiments of methods for determining the etched titrant volume for the inverted CDR test will now be disclosed. The methods for determining the etched titrant volume are similar to the methods described above for the as received titrant volume; however, to determine the etched titrant volume, a thin layer of the interior surface of the glass container is removed by etching. The etchant for removing the thin layer of the interior surface of the glass container is the same as the etchant described above for the CDR test.

As noted above, the concentration of HF and HCl in the etchant is selected to so that the etchant etches the glass container at a desired etch rate. The desired etch rate is selected to etch a layer of the interior surface of the glass container that has a thickness from greater than or equal to 0.75 µm to less than or equal to 15 µm for a duration from greater than or equal to 1 minute to less than or equal to 60 minutes. In embodiments, the thickness of the layer of the interior surface of the glass container that is removed is from greater than or equal to 0.75 µm to less than or equal to 5 µm, such as from greater than or equal to 0.85 µm to less than or equal to 1.5 µm, or even from greater than or equal to 0.95 µm to less than or equal to 1.25 µm. In embodiments, the thickness of the layer of the interior surface of the glass container that is removed is at least 1.00 µm. In embodiments, the duration of the etching process is from greater than or equal to 1.0 minute to less than or equal to 60 minutes, such as from greater than or equal to 2.0 minutes to less than or equal to 4.0 minutes. In other embodiments, the duration of the etching process is from greater than or equal to 2.5 minutes to less than or equal to 3.5 minutes, such as about 3.0 minutes. Without being bound to any particular theory, it is believed that volatilized constituents are deposited and reincorporated on the glass container at depths up to about 500 nm. Therefore, removing more than 500 nm by etching is desired so that the titrant contacts the region of the glass container having the bulk concentration (i.e., the concentration without volatilized and deposited components). It should be understood that the etching can be conducted by placing etchant in the interior of the glass container or by submerging the glass container in an etchant bath.

According to embodiments, once the glass containers have been etched, the etchant is discarded. The glass containers are then soaked in a water bath for about 5 minutes. After all the soaking steps are complete, the glass containers are, according to some embodiments, washed at least six times with water having a conductivity of 18 MΩ-cm or more, such as purified water defined by USP <1231>, freshly distilled water, water consistent with current EP purified water [EP Chapter 4.1.1—water], water R or R1, or USP carbon dioxide-free water. In some embodiments, the glass containers are washed three times in 10 MΩ-cm water, and subsequently, the containers are washed at least three times in 10 MΩ-cm water to ensure that the etched surfaces of the glass containers are free from contaminants.

Once the glass containers have been etched and cleaned, the amount of solvent needed to determine the chemical heterogeneity of the glass container is calculated. According to embodiments, roughly the same amount of solvent should be added to the etched glass containers as was added to the as received glass containers so that the same regions of the glass containers are being measured by the titration. In embodiments, this can be achieved by filling the etched glass containers with solvent such that the solvent comprises from greater than or equal to 5.0% by volume of the glass container to less than or equal to 50.0% by volume of the glass container, such as from greater than or equal to 6.0% by volume of the glass container to less than or equal to 35.0% by volume of the glass container from greater than or equal to 8.0% by volume of the glass container to less than or equal to 25.0% by volume of the glass container, from greater than or equal to 9.0% by volume of the glass container to less than or equal to 15% by volume of the glass container, or even from greater than or equal to 10.0% by volume of the glass container to less than or equal to 14.0% by volume of the glass container. In other embodiments, the etched glass containers may be filled with solvent such that the solvent comprises from greater than or equal to 11.0% by volume of the glass container to less than or equal to 13.0% by volume of the glass container, such as about 12.5% by volume of the glass container. The amount of solvent that is required to fill the etched glass container to the required percentage is calculated by filling at least 6 etched glass containers to brimful capacity and averaging the brimful capacity of the at least 6 etched glass containers. This average brimful capacity can then be used to calculate the actual volume of solvent that will be added to the glass container to correspond to the desired percentage. In embodiments, the solvent is high purity water. In some embodiments, the solvent may be an acid, a base, or glycine.

In embodiments, the total number of etched glass containers to be tested will be determined based upon the actual volume of solvent that is added to the glass containers and the volume of solution needed to perform the titration. In some embodiments, the titration will require greater than or equal to 25 mL of solution, such as greater than or equal to 40 mL of solution, or even greater than or equal to 45 mL of solution. In some embodiments, the titration will require greater than or equal to 50 mL of solution, such as greater than or equal to 60 mL of solution, or even greater than or equal to 100 mL of solution. It should be understood that excess solution (i.e., more than the amount of solution needed to perform the titration) may be formed, and then the amount of solution needed to run the titration can be separated from the excess solution. The number of etched glass containers to be tested can be determined by dividing the volume required for the titration by the actual volume of solvent added to each glass container.

The number of etched glass containers to be tested, as determined by the foregoing calculation, are filled with the desired percentage of solvent and plugged with a water tight plug as described above. The plugged, etched glass containers are then put into an inverted position and heated to a temperature from greater than or equal to 90° C. to less than or equal to 130° C., such as from greater than or equal to 95° C. to less than or equal to 125° C. In some embodiments, the heating includes placing the containers, in their inverted position into an autoclave containing water at ambient temperature. Once the autoclave is loaded with the plugged, etched glass containers, it is heated to about 100° C. and steam is permitted to issue from the vent cock for about 10 minutes. After the about 10 minutes has elapsed, the vent cock is closed and the autoclave is heated from about 100° C. to about 121° C. at a rate of about 1° C. per minute. The autoclave temperature is maintained at 121±1° C. for 60±1 minutes. Subsequently, the temperature of the autoclave is lowered from about 121° C. to about 100° C. at a rate of about 0.5° C. per minute with venting to prevent a vacuum from forming within the autoclave. The autoclave is allowed to then cool to about 95° C. before it is opened and the plugged, etched glass containers are removed from the autoclave in the inverted position. The plugged, etched glass containers can then be cooled in a water bath at about 80° C. that is replenished with cold running tap water. In some embodiments, a cooling plate and fans are used in place of the water bath. Regardless of whether a water bath or cooling plate is used to cool the plugged, etched glass containers, the glass containers should be cooled for less than or equal to 30 minutes, such as less than or equal to 25 minutes, or even less than or equal to 20 minutes. After cooling, the temperature of the solution in the plugged, etched glass containers should be less than or equal to 25° C., such as less than or equal to 23° C. The plugged, etched glass containers are maintained in their inverted positions throughout the cooling process.

In embodiments, in less than or equal to one hour after the plugged, etched glass containers have been removed from the autoclave, the solution is titrated. To titrate the solution, the glass containers are unplugged and the solution from each of the etched glass containers is consolidated into a single vessel using a pre-cleaned funnel. As discussed above, the volume of the consolidated amount of solution should be greater than or equal to the amount required to titrate the solution. Once consolidated, according to embodiments, the amount of the consolidated solution needed to conduct the titration is extracted and methyl red indicator is added. In embodiments, about 0.05 mL of methyl red indicator is added per 25 mL of solution.

A titration blank is formulated having substantially the same volume as the consolidated solution from the glass containers. The volume of the titration blank is substantially the same as the volume required for titrating the solution, and is formulated from high purity water with the addition of 0.05 mL of methyl red per 25 mL of high purity water.

In embodiments, the titration blank is titrated by adding 0.01 M HCl to the titration blank in a drop-wise manner. The volume of HCl required to change the color of the titration blank is recorded. The consolidated solution from the etched glass containers is titrated by adding 0.01 M HCl to the consolidated solution in a drop-wise manner. The volume of the HCl required to change the color of the consolidated solution is recorded. In some embodiments, the volume of HCl required to change the color of the titration blank is subtracted from the volume of the HCl required to change the color of the consolidated solution. The results of the titration are recorded in mL of 0.01 M HCl per 100 mL of the consolidated solution. This result is the etched titrant volume.

It should be understood that the above titration processes—both for the as received glass containers and the etched glass containers—can be automated by using a calibrated automated titration device. Such devices are well known in the art and include, as an example, a Metrohm with an 888 Titrando exchange unit (operational Apr. 25, 2014) containing an 814 USB Sample processor autosampler. The automated titration device parameters may be set as follows: 5 mL/min dosing rate; 60 second pause between additions; 0.02 mL dosing volume increase; and 25 mV/min signal drift.

Once measured, the as received titrant volume and the etched titrant volume for the inverted CDR test can then be used in Equation (1) with the as received titrant volume to obtain the CDR value of the shoulder region of the glass container. As outlined above, a CDR value near unity indicates that little to no chemical heterogeneity exists in the shoulder region of the glass container, which will have little to no delamination risk. However, the further the CDR value is from unity, the delamination risk increases.

In embodiments, when the CDR value is 0.6 or less, additional analysis may, optionally, be conducted to determine whether the low CDR value is a result of chemical heterogeneity or whether the low CDR value is a result of some other anomaly. The additional analyses may be conducted whether the standard CDR test has been conducted or the inverted CDR test has been conducted. This additional analysis may include multiple etching steps that etch thin layers of the glass container so that a titration may be performed at various etching intervals. For instance, in some embodiments, the additional analysis may include etching a 100 nm thick layer of the glass surface and then conducting the titration process, such as the titration process as disclosed above. Once the titration process is complete, the glass container may again be etched to remove an additional 100 nm thick layer of the glass container, and an additional titration process, such as the titration process disclosed above, may be conducted at a total etch depth of 200 nm. This etching followed by titrating process may be conducted multiple times until a desired thickness is removed from the glass container. As an example, and without limitation, where 100 nm thick layers are etched from the glass article, and the desired thickness to be removed from the glass container is 1 µm, ten etching and titrating steps can be conducted to reach the 1 µm desired thickness. It should be understood, that based on the thickness of the glass container and the desired thickness of the glass to be removed by etching, the etching interval in the additional analysis may vary. According to embodiments, the etching interval of the additional analysis may be from greater than or equal to 50 nm to less than or equal to 250 nm, such as from greater than or equal to 75 nm to less than or equal to 225 nm, or even from greater than or equal to 100 nm to less than or equal to 200 nm. In some embodiments, the etching interval of the additional analysis may be from greater than or equal to 125 nm to less than or equal to 175 nm, such as about 150 nm. In these embodiments, the desired thickness refers to the maximum thickness of a removed layer to which the glass container is etched. In certain embodiments, the desired thickness will be the sum of all etching processes conducted.

In embodiments where the additional analysis is conducted, there will be multiple, discrete titration volumes to be considered (i.e., at least one titration volume from each of the etching intervals and the titration at the desired thickness). In such embodiments, the maximum titration volume from the etching interval titrations and the titration volume at the desired thickness will be used to calculate the CDR. Accordingly, the CDR may be calculated by Equation (2):

$$CDR = \frac{\text{Maximum Titration Volume of the Etching Intervals}}{\text{Titration Volume at the Greatest Thickness}} \quad (2)$$

In Equation (2), the maximum titration volume of the intervals is the greatest discrete value of the titration volume for all of the intervals excluding the titration volume for the maximum etching level, and the titration volume at the greatest thickness is the titration volume measured at the highest level of etching.

In some embodiments, an object made from material other than the glass composition of the glass container may be present in a pharmaceutical packaging, such as a plunger, syringe, or integrated cap (hereinafter referred to as "the object"). When the CDR test is to be conducted on such pharmaceutical packaging, it may be necessary to separately determine the titrant volume resultant from the object and the titrant volume resultant from the glass container. In embodiments, this determination can be done by isolating the object and performing the titration. For instance, if the object is removable from the glass container, then the object can be removed, cleaned (such as by autoclaving) to see what components are extracted into a solution, and then a titration can be performed. This titration may be conducted by placing the object in a vessel that will have little to no impact on the titration results and filling the vessel with a titrant. Once the vessel is filled with a titrant, a titration may be performed as described above for the CDR test. The results of this titration may be recorded and factored into the results of the titration of the glass container in the CDR test, such as by using the results of the object titration in the same manner that a titration blank is used in the above processes. If the object is not removable from the glass container, the object may be isolated for titration by manipulating the orientation of the glass container so that the titrant mostly contacts the object. For instance, if the object is a plunger that is not removable from the glass container, titrant may be added to the glass container, and the glass container may be inverted or otherwise oriented so that the titrant mostly contacts the plunger. Once the glass container has been orientated so that the titrant mostly contacts the plunger, a titration may be performed as disclosed above for the CDR test. The results of this titration may be recorded and factored into the results of the titration of the glass container in the CDR test, such as by subtracting the results as a blank.

In the embodiments described herein, the glass containers may be formed from glass compositions which meet the criteria for Type I, Class A (Type IA) or Type I, Class B (Type IB) glasses under ASTM Standard E438-92 (2011) entitled "Standard Specification for Glasses in Laboratory Apparatus". Borosilicate glasses meet the Type I (A or B) criteria and are routinely used for pharmaceutical packaging. Examples of borosilicate glass include, without limitation, Corning® Pyrex® 7740, 7800, Wheaton 180, 200, and 400, Schott Duran®, Schott Fiolax®, KIMAX® N-51A, Gerresheimer GX-51 Flint and others.

The glass compositions from which the glass containers are formed are chemically durable and resistant to degradation, as determined by the ISO 720 standard. The ISO 720 standard is a measure of the resistance of the glass to degradation in distilled water (i.e., the hydrolytic resistance of the glass). In brief, the ISO 720 standard protocol utilizes crushed grass grains which are placed in contact with 10 MΩ-cm water under autoclave conditions (121° C., 2 atm) for 30 minutes. The solution is then titrated colorimetrically with dilute HCl to neutral pH. The amount of HCl required to titrate to a neutral solution is then converted to an equivalent of $Na_2O$ extracted from the glass and reported in 1 µg of glass with smaller values indicative of greater durability. The ISO 720 entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; ISO 720:1985 entitled "Glass—Hydrolytic resistance of glass grains at 121 degrees C.—Method of test and classification"; and ISO 719:1985 "Glass—Hydrolytic resistance of glass grains at 98 degrees C.—Method of test and classification." Each standard and the classifications standard is broken into individual types. Type HGA1 is indicative of up to 62 µg extracted equivalent of $Na_2O$; Type HGA2 is indicative of more than 62 µg and up to 527 µg extracted equivalent of $Na_2O$; and Type HGA3 is indicative of more than 527 µg and up to 930 µg extracted equivalent of $Na_2O$. The glass containers described herein have an ISO 720 type HGA1 hydrolytic resistance in the as received state.

The glass compositions from which the glass containers are formed are also chemically durable and resistant to degradation, as determined by the ISO 719 standard. The ISO 719 standard is a measure of the resistance of the glass to degradation in distilled water (i.e., the hydrolytic resistance of the glass). In brief, the ISO 719 standard protocol utilizes crushed glass grains which are placed in contact with 18 MΩ-cm water at a pressure of 2 atm and a temperature of 98° C. for 60 minutes. The solution is then titrated colorimetrically with dilute HCl to neutral pH. The amount of HCl required to titrate to a neutral solution is then converted to an equivalent of $Na_2O$ extracted from the glass and reported in 1 µg of glass with smaller values indicative of greater durability. The ISO 719 standard is broken into individual types. Type HGB1 is indicative of up to 31 µg extracted equivalent of $Na_2O$; Type HGB2 is indicative of more than 31 µg and up to 62 µg extracted equivalent of $Na_2O$; Type HGB3 is indicative of more than 62 µg and up to 264 µg extracted equivalent of $Na_2O$; Type HGB4 is indicative of more than 264 µg and up to 620 µg extracted equivalent of $Na_2O$; and Type HGB5 is indicative of more than 620 µg and up to 1085 µg extracted equivalent of $Na_2O$. The glass containers described herein have an ISO 719 type HGB1 hydrolytic resistance in the as received state.

With respect to the USP <660> test and/or the European Pharmacopeia 3.2.1 test, the glass containers described herein have a Type I chemical durability in the as received state. As noted above, the USP <660> and European Pharmacopeia 3.2.1 tests are performed on intact glass containers rather than crushed grains of glass and, as such, the USP <660> and European Pharmacopeia 3.2.1 tests may be used to directly assess the chemical durability of the interior surface of the glass containers.

The glass compositions from which the glass containers are formed are also chemically durable and resistant to degradation in acidic solutions, as determined by the DIN 12116 standard, in the as received state. In brief, the DIN 12116 standard utilizes a polished glass sample of a known surface area which is weighed and then positioned in contact with an amount of boiling 6 M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically $mg/dm^2$. The DIN 12116 standard is broken into individual classes. Class S1 indicates weight losses of up to $0.7\ mg/dm^2$; Class S2 indicates weight losses from $0.7\ mg/dm^2$ up to $1.5\ mg/dm^2$; Class S3 indicates weight losses from $1.5\ mg/dm^2$ up to $15\ mg/dm^2$; and Class S4 indicates weight losses of more than $15\ mg/dm^2$. The glass containers described herein have a DIN 12116 Class S2 acid resistance or better in the as received state.

The glass compositions from which the glass containers are formed are also chemically durable and resistant to degradation in basic solutions, as determined by the ISO 695 standard, in the as received state. In brief, the ISO 695 standard utilizes a polished glass sample which is weighed and then placed in a solution of boiling 1 M NaOH+0.5M $Na_2CO_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically $mg/dm^2$. The ISO 695 standard is broken into individual classes. Class A1 indicates weight losses of up to $75\ mg/dm^2$; Class A2 indicates weight losses from $75\ mg/dm^2$ up to $175\ mg/dm^2$; and Class A3 indicates weight losses of more than $175\ mg/dm^2$. The glass containers described herein have an ISO 695 base resistance of Class A2 or better in the as received state.

It should be understood that, when referring to the above referenced classifications according to ISO 695, ISO 719, ISO 720 or DIN 12116, a glass composition or glass container which has a specified classification "or better" means that the performance of the glass composition is as good as or better than the specified classification. For example, a glass container which has an ISO 695 base resistance of "Class A2" or better may have an ISO 695 classification of either Class A2 or Class A1.

Embodiments of the methods and apparatuses described herein will now be defined in various clauses. The following clauses are exemplary and do not limit other embodiments disclosed and described herein. It should be understood that any of the clauses described below may be combined with one or more other clauses.

A first clause comprises a method for determining a delamination risk of a plurality of glass containers, the method comprising: obtaining a plurality of glass containers, each glass container of the plurality of glass containers having a similar composition and similar geometry; adding to each glass container of the plurality of the glass containers a solvent such that a volume of the solvent in each glass container comprises from greater than or equal to 5.0% by volume of the glass container to less than or equal to 50.0% by volume of the glass container; heating the plurality of glass containers to a temperature from 90° C. to 130° C.; cooling the plurality of glass containers to room temperature; removing and consolidating the solvent from the plurality of glass containers to obtain a consolidated solvent; titrating the consolidated solvent, wherein an amount of a titrant used in titrating the consolidated solvent is an as received titrant volume; etching each glass container of the plurality of glass containers by contacting at least an interior surface of the each glass container with an etchant, wherein the etching removes a layer of the interior surface of each glass container, the layer having a thickness from greater than or equal to 0.75 µm to less than or equal to 15 µm to obtain a plurality of etched glass containers; rinsing each etched glass container of the plurality of etched glass containers to remove residual etchant; adding to each etched glass container of the plurality of etched glass containers a second solvent such that a volume of the second solvent in each etched glass container comprises from greater than or equal to 5.0% by volume of the etched glass container to less than or equal to 50.0% by volume of the etched glass container; heating the plurality of etched glass containers to temperatures from 90° C. to 130° C.; cooling the plurality of etched glass containers to room temperature; removing and consolidating the second solvent from the plurality of etched glass containers to obtain an etched consolidated solvent; titrating the etched consolidated solvent, wherein an amount of a titrant used in titrating the etched consolidated solvent is an etched titrant volume; calculating a Chemical Durability Ratio (CDR) of the plurality of glass containers where:

$$CDR = \frac{\text{As Received Titrant Volume}}{\text{Etched Titrant Volume}}.$$

A second clause comprises the method according to the first clause, wherein the solvent added to each glass container of the plurality of the glass containers comprises from greater than or equal to 8.0% by volume of the glass container to less than or equal to 25.0% by volume of the glass container, and the second solvent added to each etched glass container of the plurality of etched glass containers comprises from greater than or equal to 8.0% by volume of the glass container to less than or equal to 25.0% by volume of the etched glass container.

A third clause comprises the method according to the first and second clauses, wherein the solvent added to each glass container of the plurality of the glass containers comprises about 12.5% by volume of the glass container, and the second solvent added to each etched glass container of the plurality of etched glass containers comprises about 12.5% by volume of the glass container.

A fourth clause comprises the method according to first through third clauses, wherein at least one of the solvent and the second solvent is high purity water.

A fifth clause comprises the method according to the first through fourth clauses, further comprising discarding glass containers having a CDR from greater than 0.6 to less than 1.6.

A sixth clause comprises the method according to the first through fifth clauses, further comprising discarding glass containers having a CDR from greater than 0.8 to less than 1.2.

A seventh clause comprises the method according to the first through sixth clauses, wherein a number of glass containers comprising the plurality of glass containers is from greater than or equal to 10 glass containers to less than or equal to 300 glass containers.

An eighth clause comprises the method according to the first through seventh clauses, wherein the etching is conducted to remove a layer having a thickness from greater than or equal to 0.75 μm to less than or equal to 5 μm.

A ninth clause comprises the method according to the first through eighth clauses, wherein after the CDR is determined, the method further comprises: (a) etching a second plurality of glass containers by adding an etchant to each container of the second plurality of glass containers, wherein the etching removes a layer of an interior surface of each container of the second plurality of containers, the layer having a thickness from greater than or equal to 50 nm to less than or equal to 250 nm; (b) rinsing each glass container of the second plurality of glass containers to remove residual etchant; (c) adding to each glass container of the second plurality of glass containers a third solvent such that a volume of the third solvent in each glass container of the second plurality of glass containers comprises from greater than or equal to 5.0% by volume of a glass container of the second plurality of glass containers to less than or equal to 50.0% by volume of a glass container of the second plurality of the glass containers; (d) heating the second plurality of glass containers to a temperature from 90° C. to 130° C.; (e) cooling the second plurality of glass containers to room temperature; (f) removing and consolidating the third solvent from the second plurality of etched glass containers to obtain a second etched consolidated solvent; (g) titrating the second etched consolidated solvent, wherein an amount of a titrant used in titrating the second etched consolidated solvent is a titration volume of an interval; (h) repeating (a)-(g) until a total thickness of the interior surface of the glass container removed by etching is from greater than or equal to 0.75 μm to less than or equal to 15 μm; (i) calculating a second Chemical Durability Ratio (CDR) of the plurality of glass containers where:

$$CDR = \frac{\text{Maximum Titration Volume of the Intervals}}{\text{Titration Volume at the Greatest Thickness}}.$$

A tenth clause comprises the method according to the first through ninth clauses, wherein the glass container is a pharmaceutical package.

An eleventh clause comprises the method according to the first through tenth clauses, wherein the glass container has a Type I hydrolytic resistance according to USP <660>.

A twelfth clause comprises the method according to the first through eleventh clauses, wherein heating the plurality of glass containers comprises: placing the plurality of glass containers into an autoclave; heating the autoclave to about 100° C.; holding the autoclave at about 100° C. for about 10 minutes; heating the autoclave from about 100° C. to about 121° C. at a rate of about 1° C. per minute; holding the autoclave at about 121° C. for about 60 minutes; and cooling the autoclave from about 121° C. to about 100° C. at a rate of about 0.5° C. per minute.

A thirteenth clause comprises the method according to the twelfth clause, wherein heating the plurality of etched glass containers comprises: placing the plurality of etched glass containers into an autoclave; heating the autoclave to about 100° C.; holding the autoclave at about 100° C. for about 10 minutes; heating the autoclave from about 100° C. to about 121° C. at a rate of 1° C. per minute; holding the autoclave at about 121° C. for about 60 minutes; and cooling the autoclave from about 121° C. to about 100° C. at a rate of 0.5° C. per minute.

A fourteenth clause comprises the method according to the first through thirteenth clauses, wherein the consolidated solvent and the etched consolidated solvent are titrated with 0.01 M HCl.

A fifteenth clause comprises the method according to the first through fourteenth clauses, wherein the plurality of glass containers comprise objects having a composition that is different from the composition of the glass containers, and the method further comprises: isolating the objects in an object vessel; adding an object solvent to the object vessel; heating the objects and the object solvent to a temperature from 90° C. to 130° C.; cooling the objects and object solvent to room temperature; consolidating the solvent to obtain a consolidated object solvent; titrating the consolidated object solvent, wherein an amount of a titrant used in titrating the consolidated object solvent is an object titrant volume; modifying the CDR based on the object titrant volume.

A sixteenth clause comprises a method for determining a delamination risk of a plurality of glass containers, the method comprising: obtaining a plurality of glass containers, each glass container of the plurality of glass containers having a similar composition and similar geometry; adding to each glass container of the plurality of the glass containers a solvent such that a volume of the solvent in each glass container comprises from greater than or equal to 5.0% by volume of the glass container to less than or equal to 50.0% by volume of the glass container; plugging each container of the plurality of the glass containers with a water tight plug; inverting each container of the plurality of the glass containers; heating the plurality of glass containers to a temperature from 90° C. to 130° C.; cooling the plurality of glass containers to room temperature; removing and consolidating the solvent from the plurality of glass containers to obtain a consolidated solvent; titrating the consolidated solvent, wherein an amount of a titrant used in titrating the consolidated solvent is an as received titrant volume; etching each glass container of the plurality of glass containers by contacting an etchant with at least an interior surface of each glass container, wherein the etching removes a layer of the interior surface of each glass container, the layer having a thickness from greater than or equal to 0.75 μm to less than or equal to 15 μm to obtain a plurality of etched glass containers; rinsing each etched glass container of the plurality of etched glass containers to remove residual etchant; adding to each etched glass container of the plurality of etched glass containers a second solvent such that a volume of the second solvent in each etched glass container comprises from greater than or equal to 5.0% by volume of the etched glass container to less than or equal to 50.0% by volume of the etched glass container; plugging each container of the plurality of the glass containers with a water tight plug; inverting each container of the plurality of the glass containers; heating the plurality of etched glass containers to temperatures from 90° C. to 130° C.; cooling the plurality of etched glass containers to room temperature; removing the water tight plug and consolidating the second solvent from the plurality of etched glass containers to obtain an etched consolidated solvent; titrating the etched consolidated solvent, wherein an amount of a titrant used in titrating the etched consolidated solvent is an etched titrant volume; calculating a Chemical Durability Ratio (CDR) of the plurality of glass containers where:

$$CDR = \frac{As\ Recieved\ Titrant\ Volume}{Etched\ Titrant\ Volume}.$$

A seventeenth clause comprises the method according to the sixteenth clause, wherein the solvent added to each glass container of the plurality of the glass containers comprises from greater than or equal to 8.0% by volume of the glass container to less than or equal to 25.0% by volume of the glass container, and the second solvent added to each etched glass container of the plurality of etched glass containers comprises from greater than or equal to 8.0% by volume of the glass container to less than or equal to 25.0% by volume of the etched glass container.

An eighteenth clause comprises the method according to the sixteenth through seventeenth clauses, wherein the solvent added to each glass container of the plurality of the glass containers comprises about 12.5% by volume of the glass container, and the second solvent added to each etched glass container of the plurality of etched glass containers comprises about 12.5% by volume of the glass container.

A nineteenth clause comprises the method according to the sixteenth through eighteenth clauses, further comprising discarding glass containers having a CDR from greater than 0.6 to less than 1.6.

A twentieth clause comprises the method according to the sixteenth through nineteenth clauses, wherein the etching is conducted to remove a layer having a thickness from greater than or equal to 0.85 µm to less than or equal to 1.15 µm.

A twenty first clause comprises a method for determining a delamination risk of a plurality of glass pharmaceutical containers comprising: calculating a Chemical Durability Ratio (CDR) by comparing a property of the plurality of glass pharmaceutical containers in an as-formed condition to the property of the plurality of glass pharmaceutical containers in an etched condition; and assessing a high delamination risk to the plurality of glass pharmaceutical containers if the CDR is greater than or equal to 3.0.

A twenty second clause comprises the method according to the twenty first clause, wherein each glass pharmaceutical container of the plurality of glass pharmaceutical containers has a similar composition and similar geometry, and calculating the CDR comprises: adding to each glass pharmaceutical container of the plurality of the glass pharmaceutical containers a solvent such that a volume of the solvent in each glass pharmaceutical container comprises from greater than or equal to 5.0% by volume of the glass pharmaceutical container to less than or equal to 50.0% by volume of the glass pharmaceutical container; heating the plurality of glass pharmaceutical containers to a temperature from 90° C. to 130° C.; cooling the plurality of glass pharmaceutical containers to room temperature; removing and consolidating the solvent from the plurality of glass pharmaceutical containers to obtain a consolidated solvent; titrating the consolidated solvent, wherein an amount of a titrant used in titrating the consolidated solvent is an as received titrant volume; etching each glass pharmaceutical container of the plurality of glass pharmaceutical containers by contacting at least an interior surface of the each glass pharmaceutical container with an etchant, wherein the etching removes a layer of the interior surface of each glass pharmaceutical container, the layer having a thickness from greater than or equal to 0.75 µm to less than or equal to 15 µm to obtain a plurality of etched glass pharmaceutical containers; rinsing each etched glass pharmaceutical container of the plurality of etched glass pharmaceutical containers to remove residual etchant; adding to each etched glass pharmaceutical container of the plurality of etched glass pharmaceutical containers a second solvent such that a volume of the second solvent in each etched glass pharmaceutical container comprises from greater than or equal to 5.0% by volume of the etched glass pharmaceutical container to less than or equal to 50.0% by volume of the etched glass pharmaceutical container; heating the plurality of etched glass pharmaceutical containers to temperatures from 90° C. to 130° C.; cooling the plurality of etched glass pharmaceutical containers to room temperature; removing and consolidating the second solvent from the plurality of etched glass pharmaceutical containers to obtain an etched consolidated solvent; titrating the etched consolidated solvent, wherein an amount of a titrant used in titrating the etched consolidated solvent is an etched titrant volume; calculating the CDR of the plurality of glass pharmaceutical containers where:

$$CDR = \frac{As\ Received\ Titrant\ Volume}{Etched\ Titrant\ Volume}.$$

A twenty third clause comprises the method according to the any one of the twenty first and twenty second clauses, wherein the solvent added to each glass pharmaceutical container of the plurality of the glass pharmaceutical containers comprises from greater than or equal to 8.0% by volume of the glass pharmaceutical container to less than or equal to 25.0% by volume of the glass pharmaceutical container, and the second solvent added to each etched glass pharmaceutical container of the plurality of etched glass pharmaceutical containers comprises from greater than or equal to 8.0% by volume of the glass pharmaceutical container to less than or equal to 25.0% by volume of the etched glass pharmaceutical container.

A twenty fourth clause comprises the method according to any one of the twenty first to twenty third clauses, wherein the solvent added to each glass pharmaceutical container of the plurality of the glass pharmaceutical containers comprises about 12.5% by volume of the glass pharmaceutical container, and the second solvent added to each etched glass pharmaceutical container of the plurality of etched glass pharmaceutical containers comprises about 12.5% by volume of the glass pharmaceutical container.

A twenty fifth clause comprises the method according to any one of the twenty first to twenty fourth clauses, wherein at least one of the solvent and the second solvent is high purity water.

A twenty sixth clause comprises the method according to any one of the twenty first to twenty fifth clauses, further comprising discarding glass pharmaceutical containers having a CDR less than 0.6 or greater than 1.6.

A twenty seventh clause comprises the method according to any one of the twenty first to twenty sixth clauses, further comprising discarding glass pharmaceutical containers having a CDR less than 0.8 or greater than 1.2.

A twenty eighth clause comprises the method according to any one of the twenty first to twenty seventh clauses, wherein a number of glass pharmaceutical containers comprising the plurality of glass pharmaceutical containers is from greater than or equal to 10 glass pharmaceutical containers to less than or equal to 300 glass pharmaceutical containers.

A twenty ninth clause comprises the method according to any one of the twenty first to twenty eighth clauses, wherein the etching is conducted to remove a layer having a thickness from greater than or equal to 0.75 µm to less than or equal to 5 µm.

A thirtieth clause comprises the method according to any one of the twenty first to twenty ninth clauses, wherein after the CDR is determined, the method further comprises: (a) etching a second plurality of glass pharmaceutical containers by adding an etchant to each glass pharmaceutical container of the second plurality of glass pharmaceutical containers, wherein the etching removes a layer of an interior surface of each glass pharmaceutical container of the second plurality of glass pharmaceutical containers, the layer having a thickness from greater than or equal to 50 nm to less than or equal to 250 nm; (b) rinsing each glass pharmaceutical container of the second plurality of glass pharmaceutical containers to remove residual etchant; (c) adding to each glass pharmaceutical container of the second plurality of glass pharmaceutical containers a third solvent such that a volume of the third solvent in each glass pharmaceutical container of the second plurality of glass pharmaceutical containers comprises from greater than or equal to 8.0% by volume of a glass pharmaceutical container of the second plurality of glass pharmaceutical containers to less than or equal to 25.0% by volume of a glass pharmaceutical container of the second plurality of the glass pharmaceutical containers; (d) heating the second plurality of glass pharmaceutical containers to a temperature from 90° C. to 130° C.; (e) cooling the second plurality of glass pharmaceutical containers to room temperature; (f) removing and consolidating the third solvent from the second plurality of etched glass pharmaceutical containers to obtain a second etched consolidated solvent; (g) titrating the second etched consolidated solvent, wherein an amount of a titrant used in titrating the second etched consolidated solvent is a titration volume of an interval; (h) repeating (a)-(g) until a total thickness of the interior surface of the glass pharmaceutical container removed by etching is from greater than or equal to 0.75 µm to less than or equal to 15 µm; (i) calculating a second Chemical Durability Ratio (CDR) of the plurality of glass pharmaceutical containers where:

$$CDR = \frac{\text{Maximum Titration Volume of the Intervals}}{\text{Titration Volume at the Greatest Thickness}}.$$

A thirty first clause comprises the method according to any one of the twenty first to thirtieth clauses, wherein the glass pharmaceutical container has a Type I hydrolytic resistance according to USP <660>.

A thirty second clause comprises the method according to any one of the twenty first to thirty first clauses, wherein heating the plurality of glass pharmaceutical containers comprises: placing the plurality of glass pharmaceutical containers into an autoclave; heating the autoclave to about 100° C.; holding the autoclave at about 100° C. for about 10 minutes; heating the autoclave from about 100° C. to about 121° C. at a rate of about 1° C. per minute; holding the autoclave at about 121° C. for about 60 minutes; and cooling the autoclave from about 121° C. to about 100° C. at a rate of about 0.5° C. per minute.

A thirty third clause comprises the method according to any one of the twenty first to thirty second clauses, wherein heating the plurality of etched glass pharmaceutical containers comprises: placing the plurality of etched glass pharmaceutical containers into an autoclave; heating the autoclave to about 100° C.; holding the autoclave at about 100° C. for about 10 minutes; heating the autoclave from about 100° C. to about 121° C. at a rate of 1° C. per minute; holding the autoclave at about 121° C. for about 60 minutes; and cooling the autoclave from about 121° C. to about 100° C. at a rate of 0.5° C. per minute.

A thirty fourth clause comprises the method according to any one of the twenty first to thirty third clauses, wherein the consolidated solvent and the etched consolidated solvent are titrated with 0.01 M HCl.

A thirty fifth clause comprises the method according to any one of the twenty first to thirty fourth clauses, wherein the plurality of glass pharmaceutical containers comprise objects having a composition that is different from the composition of the glass pharmaceutical containers, and the method further comprises: isolating the objects in an object vessel; adding an object solvent to the object vessel; heating the objects and the object solvent to a temperature from 90° C. to 130° C.; cooling the objects and object solvent to room temperature; consolidating the solvent to obtain a consolidated object solvent; titrating the consolidated object solvent, wherein an amount of a titrant used in titrating the consolidated object solvent is an object titrant volume; and modifying the CDR based on the object titrant volume.

EXAMPLES

Embodiments will be further clarified by the following example for measuring the CDR of glass containers.

Example 1

Six types of glass containers were obtained for this example. Container 1 is a 3 mL alkali aluminosilicate glass container manufactured by Corning Incorporated; Container 2 is a 3 mL borosilicate glass container manufactured by Gerresheimer AG; Container 3 is a 3 mL borosilicate glass container manufactured by Schott AG that has been converted by OMPI; Container 4 is a 2 mL glass container manufactured by Schott AG; Container 5 is a 3 mL glass container; and Container 6 is a molded 3 mL glass container manufactured by Gerresheimer AG.

Initially, each of the glass containers were rinsed three times with high purity water Once the glass containers had been rinsed, high purity water was added to fill each container to 12.5 percent by volume with excess for evaporation. For the 3 mL glass containers, 0.60 mL of high purity water was added to each container, and for the 2 mL glass containers, 0.50 mL of high purity water was added to each container. Using these actual fill volumes, the number of glass containers that need to be filled to 12.5 volume percent for each of the 6 types of glass containers was calculated. For the Glass containers 1-3, 5, and 6 it was calculated that 100 glass containers for each glass container type needed to be filled to obtain the 50 mL of solution needed for the titration (i.e., 50 mL/0.60 mL per container). For the Glass container 4 it was calculated that 120 glass containers needed to be filled to obtain the 50 mL of solution needed for the titration (i.e., 50 mL/0.50 mL per container). After adding the high purity water, a petri dish was placed on the opening of each glass container and the glass containers were placed into an autoclave.

Once the autoclave was loaded with the glass containers, it was closed and heated to 100° C. and steam was permitted to issue from the vent cock for 10 minutes. After the 10 minutes had elapsed, the vent cock was closed and the autoclave was heated from 100° C. to 121° C. at a rate of 1° C. per minute. The autoclave temperature was maintained at 121±1° C. for 60 minutes. Subsequently, the temperature of the autoclave was lowered from 121° C. to 100° C. at a rate of 0.5° C. per minute with venting to prevent a vacuum from forming within the autoclave. The autoclave was allowed to cool to 95° C. before it was opened and the 6 glass containers were removed from the autoclave. The glass containers were then cooled to 25° C. in approximately 20 minutes.

Figure 3:
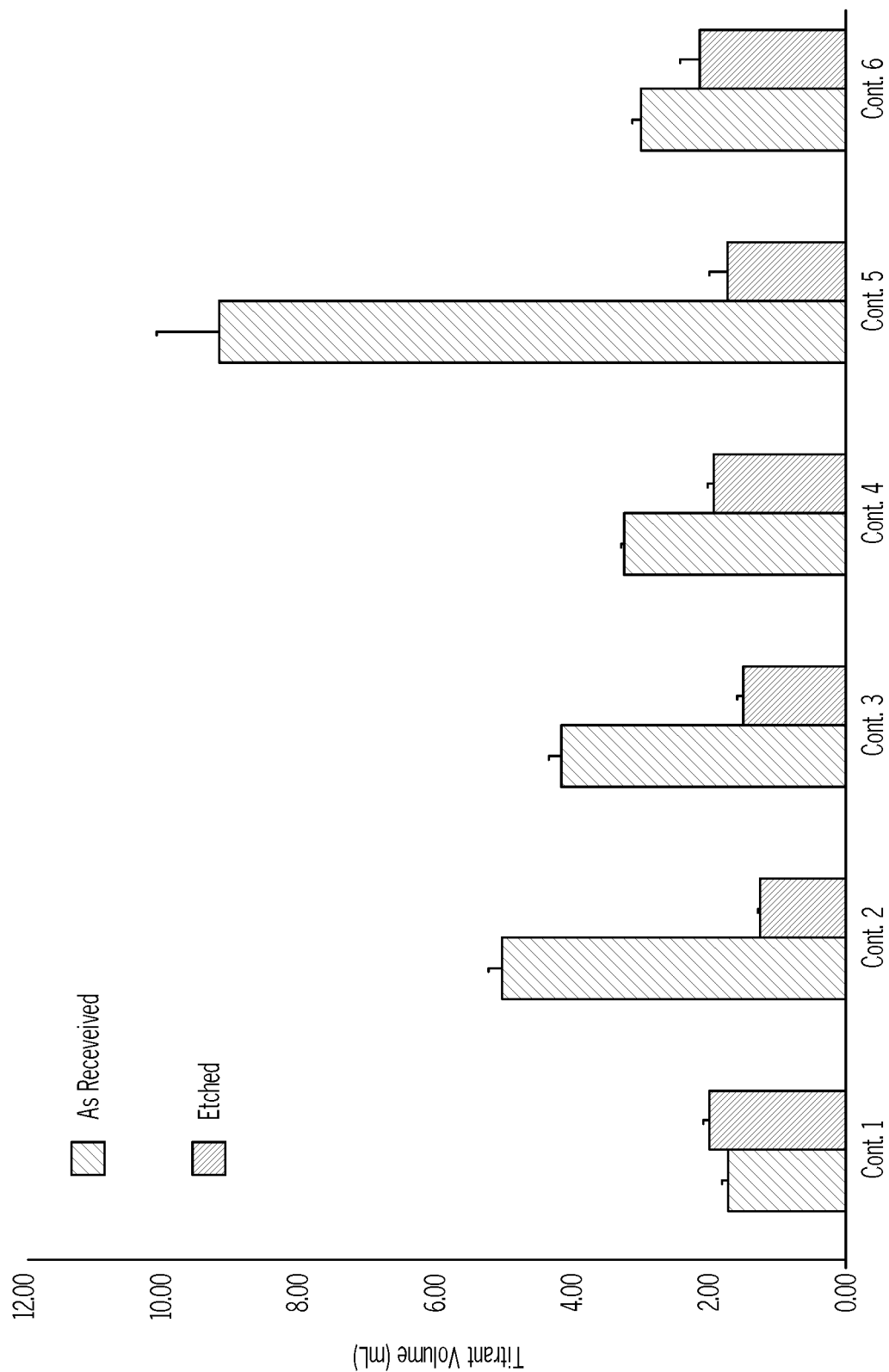
FIG. 3 graphically depicts as received titrant volume and etched titrant volume for six sample types of containers tested at a fill volume of 12.5% according to one or more embodiments disclosed and described herein.

The solution from each type of glass container was consolidated into six different vessels—one vessel for each type of glass container—using a pre-cleaned funnel. Once consolidated, 50 mL of each of the six consolidated solutions was separated from the excess liquid and pipeted into a preleached 100 mL beaker. To each solution, 100 μL of indicator was added and each were separately titrated using a Metrohm titrator with an 888 Titrando exchange unit (operational Apr. 25, 2014) containing an 814 USB Sample processor autosampler. The automated titration device parameters may be set as follows: 5 mL/min dosing rate; 60 second pause between additions; 0.02 mL dosing volume increase; and 25 mV/min signal drift. The lines of the automated titration device were flushed to remove bubbles, and 0.01 M HCl as the titrant. The results of the titration for each of the six types of glass containers was recorded as the as received titration volume. The results of these titrations are shown in the bar graph of FIG. 3 and Table 1 below. The titration for each of the 6 types of glass container was repeated in triplicate to ensure reliability of the results.

Once the as received titration volume was recorded, the etched titration volume was determined. Each of the glass containers tested above were rinsed and etched using a mixture of 2 M HF and 3 M HCl as the etchant. The vials were completely submerged in an etchant bath containing between 200-500 mL of etchant, and ensuring that all the glass containers are completely submerged and filled. The glass containers were etched by the etchant for three minutes.

Once the glass containers were etched, they were soaked in a water bath for 5 minutes. After the 5 minute soak time was complete, the glass containers were soaked in a second water bath for 5 minutes. After the second soaking step was complete, the glass containers were washed three times in 16 MΩ-cm water. Subsequently, the glass containers were washed at least three times in 18 MΩ-cm water.

Once the glass containers had been etched and cleaned, high purity water was added to fill each container to 12.5 percent by volume with excess to account for evaporation. For the 3 mL glass containers, 0.60 mL of high purity water was added to each container, and for the 2 mL glass containers, 0.50 mL of high purity water was added to each container. After adding the high purity water, a petri dish was placed on the opening of each glass container and the glass containers were placed into an autoclave.

Once the autoclave was loaded with the etched glass containers, it was heated to 100° C. and steam was permitted to issue from the vent cock for 10 minutes. After the 10 minutes had elapsed, the vent cock was closed and the autoclave was heated from 100° C. to 121° C. at a rate of 1° C. per minute. The autoclave temperature was maintained at 121±1° C. for 60 minutes. Subsequently, the temperature of the autoclave was lowered from 121° C. to 100° C. at a rate of 0.5° C. per minute with venting to prevent a vacuum from forming within the autoclave. The autoclave was allowed to cool to 95° C. before it was opened and the glass containers were removed from the autoclave. The glass containers were then cooled on a cooling plate with an external chiller. The glass containers were cooled on the cooling plate for approximately 20 minutes.

The solution from each type of etched glass container was consolidated into six different vessels—one vessel for each type of glass container—using a pre-cleaned funnel. Once consolidated, 50 mL of each of the six consolidated solutions were separately titrated using a Metrohm titrator with an 888 Titrando exchange unit (operational Apr. 25, 2014) containing an 814 USB Sample processor autosampler. The automated titration device parameters may be set as follows: 5 mL/min dosing rate; 60 second pause between additions; 0.02 mL dosing volume increase; and 25 mV/min signal drift. The lines of the automated titration device were flushed to remove bubbles, and 0.01 M HCl as the titrant. The result of the titration for each of the six types of glass containers was recorded as the etched titration volume. The results of these titrations are shown in the bar graph of FIG. 3 and in Table 1 below. The titration for each of the 6 types of glass container was repeated in triplicate to ensure reliability of the results.

TABLE 1

|  | 12.5% Fill As Received | 12.5% Fill Etched | 12.5% Fill As Received SD | 12.5% Fill Etched SD |
|---|---|---|---|---|
| Cont. 1 | 1.690 | 1.970 | 0.08 | 0.04 |
| Cont. 2 | 5.000 | 1.215 | 0.20 | 0.00 |
| Cont. 3 | 4.100 | 1.440 | 0.20 | 0.04 |
| Cont. 4 | 3.170 | 1.840 | 0.03 | 0.08 |
| Cont. 5 | 9.100 | 1.600 | 0.90 | 0.30 |
| Cont. 6 | 2.900 | 2.000 | 0.10 | 0.30 |

The as received titration volume and the etched titration volume obtained as disclosed above were then used in Equation (1) to calculate the CDR value of the glass containers. The results of these tests are provided in Table 2 below.

TABLE 2

|  | Chemical Durability Ratio for 12.5% Fill Volume | Standard Deviation Associated with Replicates for Durability Ratio |
|---|---|---|
| Container 1 | 0.9 | 0.1 |
| Container 2 | 4.1 | 0.1 |
| Container 3 | 2.9 | 0.2 |
| Container 4 | 1.7 | 0.1 |
| Container 5 | 6.0 | 1.0 |
| Container 6 | 1.5 | 0.2 |

Comparative Example 1

A comparison of the results of Example 1 to a standard test that fills the glass containers to 90.0 volume percent is provided. Container 7 is a 3 mL alkali aluminosilicate glass container manufactured by Corning Incorporated; Container 8 is a 3 mL borosilicate glass container manufactured by Gerresheimer AG; Container 9 is a 3 mL borosilicate glass container manufactured by Schott AG that has been converted by OMPI; Container 10 is a 2 mL glass container manufactured by Schott AG; Container 11 is a 3 mL molded glass container; and Container 12 is a 3 mL glass container manufactured by Gerresheimer AG.

Initially, each of the glass containers were rinsed three times with high purity water Once the glass containers had been rinsed, high purity water was added to fill each container to 90.0 percent by volume with excess to account for evaporation. For the 3 mL glass containers, 4.3 mL of high purity water was added to each container, and for the 2 mL glass containers, 4.0 mL of high purity water was added to each container. Using these actual fill volumes, the number of glass containers that need to be filled to 90.0 volume percent for each of the 6 types of glass containers was calculated. For the Glass containers 1-3, 5, and 6 it was calculated that 15 glass containers for each glass container type needed to be filled to obtain the 50 mL of solution needed for the titration (i.e., 50 mL/4.3 mL per container). For the Glass container 4 it was calculated that 20 glass containers needed to be filled to obtain the 50 mL of solution needed for the titration (i.e., 50 mL/4.0 mL per container). After adding the high purity water, a petri dish was placed on the opening of each glass container and the glass containers were placed into an autoclave.

Figure 4:
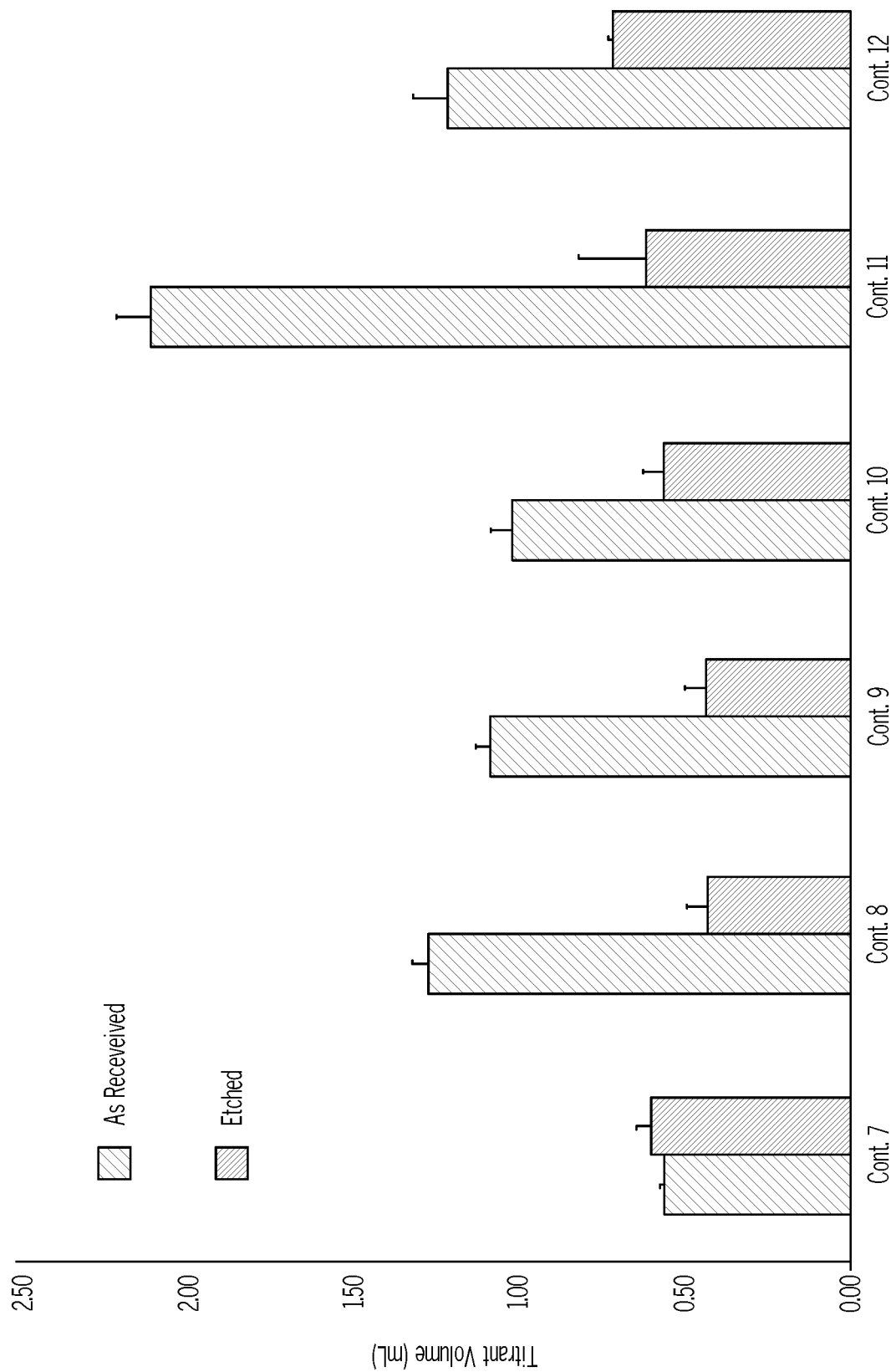
FIG. 4 graphically depicts as received titrant volume and etched titrant volume for six sample types of containers tested at a fill volume of 90.0% according to embodiments disclosed and described herein.

Containers 7-12 were autoclaved and titrated in the same manner as Containers 1-6 above to obtain the as received titration volume. Subsequently, the etched titration volume for Containers 7-12 were obtained in the same manner as for Containers 1-6, with the exception that 90.0 volume percent of solution was added to Containers 7-12 after they had been etched. The titration results obtained were used as the etched titration volume. The results of the as received and etch titration volumes are provided in FIG. 4 and Table 3 below.

TABLE 3

|  | 90% Fill As Received | 90% Fill Etched | 90% Fill As Received SD | 90% Fill Etched SD |
| --- | --- | --- | --- | --- |
| Cont. 7 | 0.56 | 0.6 | 0.01 | 0.04 |
| Cont. 8 | 1.27 | 0.42 | 0.04 | 0.06 |
| Cont. 9 | 1.08 | 0.42 | 0.04 | 0.06 |
| Cont. 10 | 1.01 | 0.55 | 0.06 | 0.06 |
| Cont. 11 | 2.1 | 0.6 | 0.1 | 0.2 |
| Cont. 12 | 1.2 | 0.7 | 0.1 | 0.01 |

The as received titration volume and the etched titration volume obtained as disclosed above were then used in Equation (1) to calculate the USP <660>-like surface testing and USP <660>-like etching test value of the glass containers. The results of these tests are provided in Table 4 below.

TABLE 4

|  | USP <660>-like Surface Glass Testing and USP <660>-like Etching Test Results | Standard Deviation Associated with Replicates for Durability Ratio |
| --- | --- | --- |
| Container 7 | 0.9 | 0.1 |
| Container 8 | 3.1 | 0.4 |
| Container 9 | 2.7 | 0.3 |
| Container 10 | 1.8 | 0.2 |
| Container 11 | 4 | 1 |
| Container 12 | 1.7 | 0.1 |

As can be determined by an examination of the Example and the Comparative Example, results of the Chemical Durability Ratio is magnified in the 12.5% low fill volume case.

Example 2

Figure 5:
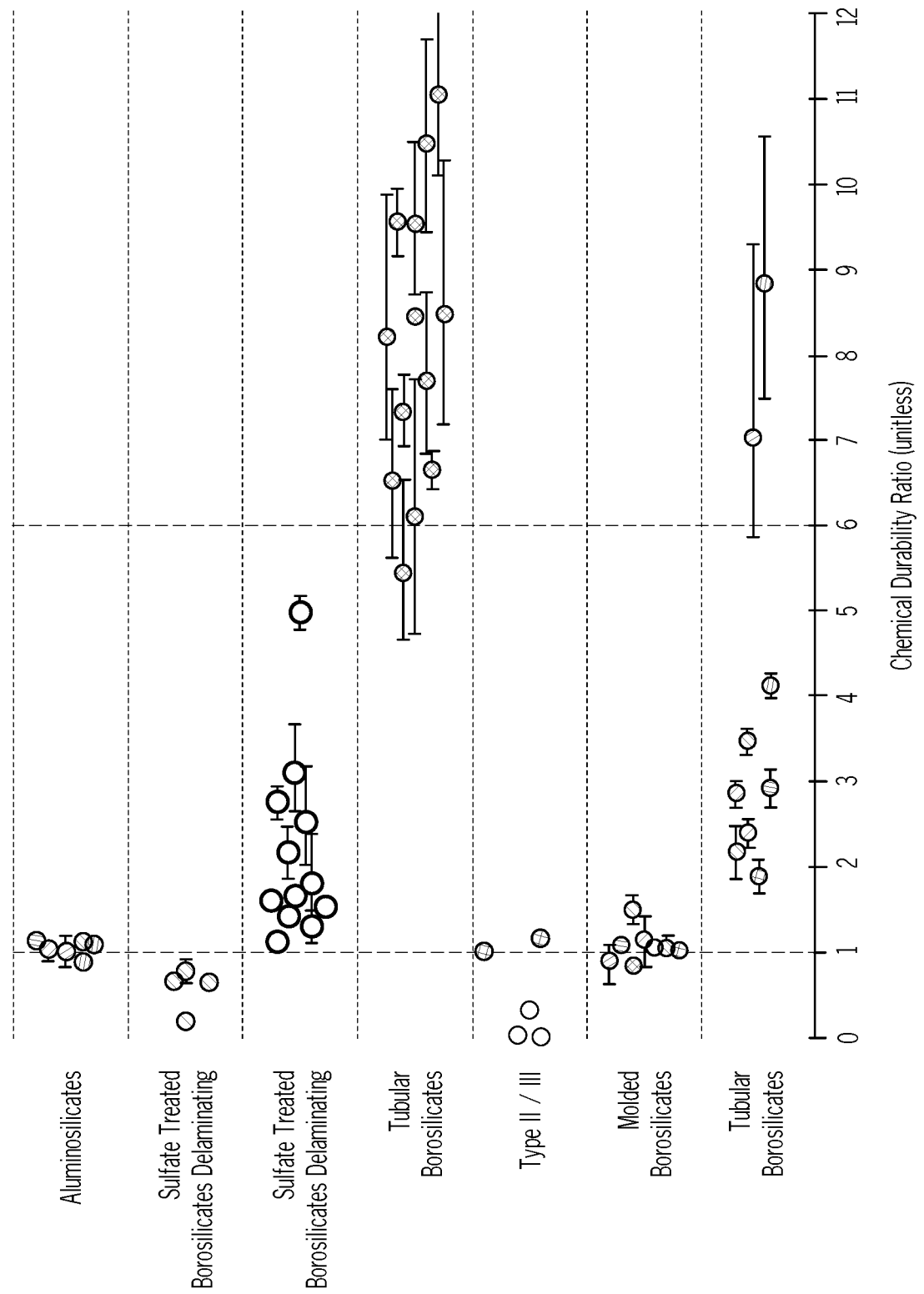
FIG. 5 graphically depicts CDR values for various pedigrees of glass containers according to embodiments disclosed and described herein.

The above-described CDR measurement was conducted on various commercially available and pharmaceutically-relevant glass container pedigrees. FIG. 5 summarizes more than 50 individual CDR measurements and groups the results by container type (shown on the y-axis with arbitrary arrangement). In the bottommost grouping, standard tubular borosilicate containers show a broad range of CDR values from about 2 to about 9. The error bars shown in the figure represent the maximum and minimum CDR values that could be obtained via the replicates for that pedigree (maximum as-received÷minimum etched=maximum error bar, and minimum as-received÷maximum etched=minimum error bar). The results show that thicker container walls tend to exhibit greater CDR values (1.2 mm & 1.5 mm wall containers resulted in a CDR value from 7-9, compared to 1.0 mm & 1.1 mm wall containers that resulted in a CDR value from 2-4). This difference in CDR value is consistent with the greater heat required for forming the thicker wall vials.

Molded borosilicate containers exhibit far less surface chemistry alteration during forming compared to tubular containers, as discussed in USP <1660>. FIG. 5 shows CDR results for a wide range of molded borosilicate containers that are consistently between 0.8 and 1.5. The containers tested include nominal volumes from 5 to >1000 mL, and both clear and amber compositions. This observation of more homogeneous surface chemistry and therefore homogeneous durability (CDR values near 1.0) is consistent with the lower delamination risk associated with molded containers.

Molded soda-lime silicate containers (USP <660> Type III) exhibit CDR values near 1.0; indicating that their surfaces are chemically homogeneous. Treated soda-lime silicate containers (USP <660> Type II) exhibit CDR values much less than 1.0, indicating that their surfaces are much different than the underlying glass. Since soda lime silicate glass has extremely low chemical durability relative to Type I glass. Thus, these glasses may not be suitable for many pharmaceutical uses.

Testing of more than ten pedigrees of delaminating tubular borosilicate containers showed that at a CDR value greater than or equal to 6.0, containers are at high risk of exhibiting delamination. Additionally, one container with a CDR value less than 6.0 exhibited delamination, but one container with a CDR value of about 5.0 did not exhibit delamination. Thus, according to this example, all tested vials with a CDR value greater than 6.0 exhibited delamination.

Vials created under identical conditions but with subsequent ammonium sulfate treatment were examined and exhibited substantially lower CDR values, such as between 1.0 and 5.0. As noted in more detail above, sulfate treated borosilicate containers cannot be assessed directly by this method, because the treatment masks the heterogeneities of interest. If CDR performance is assessed prior to sulfate treatment and the CDR value is low (e.g. less than 5.0), then the sulfate treatment will not substantially increase the risk of delamination. If, however, the CDR performance assessed prior to sulfate treatment is high (e.g., greater than 5.0), then the risk of delamination remains high and these pedigrees should be avoided.

The last pedigrees examined were tubular vials of "boron-free" or "aluminosilicate glass" compositions. As illustrated in FIG. 5, these containers can exhibit CDR values close to 1.0 which indicates that the converting process induced no significant degradation in durability.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A method for determining a delamination risk of a plurality of glass containers, the method comprising:
    obtaining a plurality of glass containers, each glass container of the plurality of glass containers having a similar composition and similar geometry;
    adding to each glass container of the plurality of the glass containers a solvent such that a volume of the solvent in each glass container comprises from greater than or equal to 5.0% by volume of the glass container to less than or equal to 50.0% by volume of the glass container;
    heating the plurality of glass containers to a temperature from 90° C. to 130° C.;
    cooling the plurality of glass containers to room temperature;
    removing and consolidating the solvent from the plurality of glass containers to obtain a consolidated solvent;
    titrating the consolidated solvent, wherein an amount of a titrant used in titrating the consolidated solvent is an as received titrant volume;
    etching each glass container of the plurality of glass containers by contacting at least an interior surface of the each glass container with an etchant, wherein the etching removes a layer of the interior surface of each glass container, the layer having a thickness from greater than or equal to 0.75 μm to less than or equal to 15 μm to obtain a plurality of etched glass containers;
    rinsing each etched glass container of the plurality of etched glass containers to remove residual etchant;
    adding to each etched glass container of the plurality of etched glass containers a second solvent such that a volume of the second solvent in each etched glass container comprises from greater than or equal to 5.0% by volume of the etched glass container to less than or equal to 50.0% by volume of the etched glass container;
    heating the plurality of etched glass containers to temperatures from 90° C. to 130° C.;
    cooling the plurality of etched glass containers to room temperature;
    removing and consolidating the second solvent from the plurality of etched glass containers to obtain an etched consolidated solvent;
    titrating the etched consolidated solvent, wherein an amount of a titrant used in titrating the etched consolidated solvent is an etched titrant volume;
    calculating a Chemical Durability Ratio (CDR) of the plurality of glass containers where:

$$CDR = \frac{\text{As Received Titrant Volume}}{\text{Etched Titrant Volume}},$$

wherein the delamination risk increases as the CDR deviates from 1.0.

2. The method according to claim 1, wherein the solvent added to each glass container of the plurality of the glass containers comprises from greater than or equal to 8.0% by volume of the glass container to less than or equal to 25.0% by volume of the glass container, and
    the second solvent added to each etched glass container of the plurality of etched glass containers comprises from greater than or equal to 8.0% by volume of the glass container to less than or equal to 25.0% by volume of the etched glass container.

3. The method according to claim 1, wherein the solvent added to each glass container of the plurality of the glass containers comprises about 12.5% by volume of the glass container, and
    the second solvent added to each etched glass container of the plurality of etched glass containers comprises about 12.5% by volume of the glass container.

4. The method according to claim 1, wherein at least one of the solvent and the second solvent is high purity water.

5. The method according to claim 1, further comprising discarding glass containers having a CDR less than 0.6 or greater than 1.6.

6. The method according to claim 1, further comprising discarding glass containers having a CDR less than 0.8 or greater than 1.2.

7. The method according to claim 1, wherein a number of glass containers comprising the plurality of glass containers is from greater than or equal to 10 glass containers to less than or equal to 300 glass containers.

8. The method according to claim 1, wherein the etching is conducted to remove a layer having a thickness from greater than or equal to 0.75 μm to less than or equal to 5 μm.

9. The method according to claim 1, wherein after the CDR is determined, the method further comprises:
    (a) etching a second plurality of glass containers by adding an etchant to each glass container of the second plurality of glass containers, wherein the etching removes a layer of an interior surface of each glass container of the second plurality of glass containers, the layer having a thickness from greater than or equal to 50 nm to less than or equal to 250 nm;
    (b) rinsing each glass container of the second plurality of glass containers to remove residual etchant;
    (c) adding to each glass container of the second plurality of glass containers a third solvent such that a volume of the third solvent in each glass container of the second plurality of glass containers comprises from greater than or equal to 8.0% by volume of a glass container of the second plurality of glass containers to less than or equal to 25.0% by volume of a glass container of the second plurality of the glass containers;
    (d) heating the second plurality of glass containers to a temperature from 90° C. to 130° C.;
    (e) cooling the second plurality of glass containers to room temperature;
    (f) removing and consolidating the third solvent from the second plurality of etched glass containers to obtain a second etched consolidated solvent;

(g) titrating the second etched consolidated solvent, wherein an amount of a titrant used in titrating the second etched consolidated solvent is a titration volume of an interval;

(h) repeating (a)-(g) until a total thickness of the interior surface of the glass container removed by etching is from greater than or equal to 0.75 μm to less than or equal to 15 μm;

(i) calculating a second Chemical Durability Ratio (CDR) of the plurality of glass containers where:

$$CDR = \frac{\text{Maximum Titration Volume of the Intervals}}{\text{Titration Volume at the Greatest Thickness}}.$$

10. The method according to claim 1, wherein the plurality of glass containers are pharmaceutical packages.

11. The method according to claim 1, wherein the plurality of glass containers have a Type I hydrolytic resistance according to USP <660>.

12. The method according to claim 1, wherein heating the plurality of glass containers comprises:
   placing the plurality of glass containers into an autoclave;
   heating the autoclave to about 100° C.;
   holding the autoclave at about 100° C. for about 10 minutes;
   heating the autoclave from about 100° C. to about 121° C. at a rate of about 1° C. per minute;
   holding the autoclave at about 121° C. for about 60 minutes; and
   cooling the autoclave from about 121° C. to about 100° C. at a rate of about 0.5° C. per minute.

13. The method according to claim 12, wherein heating the plurality of etched glass containers comprises:
   placing the plurality of etched glass containers into an autoclave;
   heating the autoclave to about 100° C.;
   holding the autoclave at about 100° C. for about 10 minutes;
   heating the autoclave from about 100° C. to about 121° C. at a rate of 1° C. per minute;
   holding the autoclave at about 121° C. for about 60 minutes; and
   cooling the autoclave from about 121° C. to about 100° C. at a rate of 0.5° C. per minute.

14. The method according to claim 1, wherein the consolidated solvent and the etched consolidated solvent are titrated with 0.01 M HCl.

15. The method according to claim 1, wherein the plurality of glass containers comprise objects having a composition that is different from the composition of the glass containers, and
   the method further comprises:
      isolating the objects in an object vessel;
      adding an object solvent to the object vessel;
      heating the objects and the object solvent to a temperature from 90° C. to 130° C.;
      cooling the objects and object solvent to room temperature;
      consolidating the solvent to obtain a consolidated object solvent;
      titrating the consolidated object solvent, wherein an amount of a titrant used in titrating the consolidated object solvent is an object titrant volume;
      modifying the CDR based on the object titrant volume.

16. A method for determining a delamination risk of a plurality of glass containers, the method comprising:
   obtaining a plurality of glass containers, each glass container of the plurality of glass containers having a similar composition and similar geometry;
   adding to each glass container of the plurality of the glass containers a solvent such that a volume of the solvent in each glass container comprises from greater than or equal to 5.0% by volume of the glass container to less than or equal to 50.0% by volume of the glass container;
   plugging each glass container of the plurality of the glass containers with a water tight plug;
   inverting each glass container of the plurality of the glass containers;
   heating the plurality of glass containers to a temperature from 90° C. to 130° C.;
   cooling the plurality of glass containers to room temperature;
   removing and consolidating the solvent from the plurality of glass containers to obtain a consolidated solvent;
   titrating the consolidated solvent, wherein an amount of a titrant used in titrating the consolidated solvent is an as received titrant volume;
   etching each glass container of the plurality of glass containers by contacting an etchant with at least an interior surface of each glass container, wherein the etching removes a layer of the interior surface of each glass container, the layer having a thickness from greater than or equal to 0.75 μm to less than or equal to 15 μm to obtain a plurality of etched glass containers;
   rinsing each etched glass container of the plurality of etched glass containers to remove residual etchant;
   adding to each etched glass container of the plurality of etched glass containers a second solvent such that a volume of the second solvent in each etched glass container comprises from greater than or equal to 5.0% by volume of the etched glass container to less than or equal to 50.0% by volume of the etched glass container;
   plugging each glass container of the plurality of the glass containers with a water tight plug;
   inverting each glass container of the plurality of the glass containers;
   heating the plurality of etched glass containers to temperatures from 90° C. to 130° C.;
   cooling the plurality of etched glass containers to room temperature;
   removing the water tight plug and consolidating the second solvent from the plurality of etched glass containers to obtain an etched consolidated solvent;
   titrating the etched consolidated solvent, wherein an amount of a titrant used in titrating the etched consolidated solvent is an etched titrant volume;
   calculating a Chemical Durability Ratio (CDR) of the plurality of glass containers where:

$$CDR = \frac{\text{As \textit{Recieved} Titrant Volume}}{\text{Etched Titrant Volume}},$$

wherein the delamination risk increases as the CDR deviates from 1.0.

17. The method according to claim 16, wherein the solvent added to each glass container of the plurality of the glass containers comprises from greater than or equal to 8.0% by volume of the glass container to less than or equal to 25.0% by volume of the glass container, and the second solvent added to each etched glass container of the plurality of etched glass containers comprises from greater than or equal to 8.0% by volume of the glass container to less than or equal to 25.0% by volume of the etched glass container.

18. The method according to claim 16, wherein the solvent added to each glass container of the plurality of the glass containers comprises about 12.5% by volume of the glass container, and the second solvent added to each etched glass container of the plurality of etched glass containers comprises about 12.5% by volume of the glass container.

19. The method according to claim 16, further comprising discarding glass containers having a CDR less than 0.6 or greater than 1.6.

20. The method according to claim 16, wherein the etching is conducted to remove a layer having a thickness from greater than or equal to 0.85 μm to less than or equal to 1.15 μm.

21. A method for determining a delamination risk of a plurality of glass pharmaceutical containers comprising:
calculating a Chemical Durability Ratio (CDR) by:
adding to each glass pharmaceutical container of the plurality of the glass pharmaceutical containers a solvent such that a volume of the solvent in each glass pharmaceutical container comprises from greater than or equal to 5.0% by volume of the glass pharmaceutical container to less than or equal to 50.0% by volume of the glass pharmaceutical container;
heating the plurality of glass pharmaceutical containers to a temperature from 90° C. to 130° C.;
cooling the plurality of glass pharmaceutical containers to room temperature;
removing and consolidating the solvent from the plurality of glass pharmaceutical containers to obtain a consolidated solvent;
titrating the consolidated solvent, wherein an amount of a titrant used in titrating the consolidated solvent is an as received titrant volume;
etching each glass pharmaceutical container of the plurality of glass pharmaceutical containers by contacting at least an interior surface of the each glass pharmaceutical container with an etchant, wherein the etching removes a layer of the interior surface of each glass pharmaceutical container, the layer having a thickness from greater than or equal to 0.75 μm to less than or equal to 15 μm to obtain a plurality of etched glass pharmaceutical containers;
rinsing each etched glass pharmaceutical container of the plurality of etched glass pharmaceutical containers to remove residual etchant;
adding to each etched glass pharmaceutical container of the plurality of etched glass pharmaceutical containers a second solvent such that a volume of the second solvent in each etched glass pharmaceutical container comprises from greater than or equal to 5.0% by volume of the etched glass pharmaceutical container to less than or equal to 50.0% by volume of the etched glass pharmaceutical container;
heating the plurality of etched glass pharmaceutical containers to temperatures from 90° C. to 130° C.;
cooling the plurality of etched glass pharmaceutical containers to room temperature;
removing and consolidating the second solvent from the plurality of etched glass pharmaceutical containers to obtain an etched consolidated solvent;
titrating the etched consolidated solvent, wherein an amount of a titrant used in titrating the etched consolidated solvent is an etched titrant volume;
calculating the CDR of the plurality of glass pharmaceutical containers where:

$$CDR = \frac{\text{As Received Titrant Volume}}{\text{Etched Titrant Volume}},$$

and
assessing a delamination risk to the plurality of glass pharmaceutical containers if the CDR is greater than or equal to 3.0.

22. The method according to claim 21, wherein the solvent added to each glass pharmaceutical container of the plurality of the glass pharmaceutical containers comprises from greater than or equal to 8.0% by volume of the glass pharmaceutical container to less than or equal to 25.0% by volume of the glass pharmaceutical container, and the second solvent added to each etched glass pharmaceutical container of the plurality of etched glass pharmaceutical containers comprises from greater than or equal to 8.0% by volume of the glass pharmaceutical container to less than or equal to 25.0% by volume of the etched glass pharmaceutical container.

23. The method according to claim 21, wherein the solvent added to each glass pharmaceutical container of the plurality of the glass pharmaceutical containers comprises about 12.5% by volume of the glass pharmaceutical container, and the second solvent added to each etched glass pharmaceutical container of the plurality of etched glass pharmaceutical containers comprises about 12.5% by volume of the glass pharmaceutical container.

24. The method according to claim 21, wherein at least one of the solvent and the second solvent is high purity water.

25. The method according to claim 21, further comprising discarding glass pharmaceutical containers having a CDR less than 0.6 or greater than 1.6.

26. The method according to claim 21, further comprising discarding glass pharmaceutical containers having a CDR less than 0.8 or greater than 1.2.

27. The method according to claim 21, wherein a number of glass pharmaceutical containers comprising the plurality of glass pharmaceutical containers is from greater than or equal to 10 glass pharmaceutical containers to less than or equal to 300 glass pharmaceutical containers.

28. The method according to claim 21, wherein the etching is conducted to remove a layer having a thickness from greater than or equal to 0.75 μm to less than or equal to 5 μm.

29. The method according to claim 21, wherein after the CDR is determined, the method further comprises:
(a) etching a second plurality of glass pharmaceutical containers by adding an etchant to each glass pharmaceutical container of the second plurality of glass pharmaceutical containers, wherein the etching removes a layer of an interior surface of each glass pharmaceutical container of the second plurality of glass pharmaceutical containers, the layer having a thickness from greater than or equal to 50 nm to less than or equal to 250 nm;

(b) rinsing each glass pharmaceutical container of the second plurality of glass pharmaceutical containers to remove residual etchant;
(c) adding to each glass pharmaceutical container of the second plurality of glass pharmaceutical containers a third solvent such that a volume of the third solvent in each glass pharmaceutical container of the second plurality of glass pharmaceutical containers comprises from greater than or equal to 8.0% by volume of a glass pharmaceutical container of the second plurality of glass pharmaceutical containers to less than or equal to 25.0% by volume of a glass pharmaceutical container of the second plurality of the glass pharmaceutical containers;
(d) heating the second plurality of glass pharmaceutical containers to a temperature from 90° C. to 130° C.;
(e) cooling the second plurality of glass pharmaceutical containers to room temperature;
(f) removing and consolidating the third solvent from the second plurality of etched glass pharmaceutical containers to obtain a second etched consolidated solvent;
(g) titrating the second etched consolidated solvent, wherein an amount of a titrant used in titrating the second etched consolidated solvent is a titration volume of an interval;
(h) repeating (a)-(g) until a total thickness of the interior surface of the glass pharmaceutical container removed by etching is from greater than or equal to 0.75 μm to less than or equal to 15 μm;
(i) calculating a second Chemical Durability Ratio (CDR) of the plurality of glass pharmaceutical containers where:

$$CDR = \frac{\text{Maximum Titration Volume of the Intervals}}{\text{Titration Volume at the Greatest Thickness}}.$$

30. The method according to claim 21, wherein the plurality of glass pharmaceutical containers have a Type I hydrolytic resistance according to USP <660>.

31. The method according to claim 21, wherein heating the plurality of glass pharmaceutical containers comprises:
placing the plurality of glass pharmaceutical containers into an autoclave;
heating the autoclave to about 100° C.;
holding the autoclave at about 100° C. for about 10 minutes;
heating the autoclave from about 100° C. to about 121° C. at a rate of about 1° C. per minute;
holding the autoclave at about 121° C. for about 60 minutes; and
cooling the autoclave from about 121° C. to about 100° C. at a rate of about 0.5° C. per minute.

32. The method according to claim 31, wherein heating the plurality of etched glass pharmaceutical containers comprises:
placing the plurality of etched glass pharmaceutical containers into an autoclave;
heating the autoclave to about 100° C.;
holding the autoclave at about 100° C. for about 10 minutes;
heating the autoclave from about 100° C. to about 121° C. at a rate of 1° C. per minute;
holding the autoclave at about 121° C. for about 60 minutes; and
cooling the autoclave from about 121° C. to about 100° C. at a rate of 0.5° C. per minute.

33. The method according to claim 21, wherein the consolidated solvent and the etched consolidated solvent are titrated with 0.01 M HCl.

34. The method according to claim 21, wherein the plurality of glass pharmaceutical containers comprise objects having a composition that is different from the composition of the glass pharmaceutical containers, and the method further comprises:
isolating the objects in an object vessel;
adding an object solvent to the object vessel;
heating the objects and the object solvent to a temperature from 90° C. to 130° C.;
cooling the objects and object solvent to room temperature;
consolidating the solvent to obtain a consolidated object solvent;
titrating the consolidated object solvent, wherein an amount of a titrant used in titrating the consolidated object solvent is an object titrant volume; and
modifying the CDR based on the object titrant volume.

* * * * *